United States Patent
Sasaki et al.

(10) Patent No.: US 9,545,186 B2
(45) Date of Patent: Jan. 17, 2017

(54) ENDOSCOPE IMAGE RECORDING APPARATUS, ENDOSCOPE IMAGE ACQUISITION ASSISTING METHOD AND COMPUTER READABLE MEDIUM

(71) Applicant: FUJIFILM Corporation, Tokyo (JP)

(72) Inventors: Wataru Sasaki, Tokyo (JP); Goro Miura, Tokyo (JP); Kunimasa Shimizu, Tokyo (JP); Atsushi Misawa, Tokyo (JP); Yasuhiro Asai, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 230 days.

(21) Appl. No.: 14/495,363

(22) Filed: Sep. 24, 2014

(65) Prior Publication Data

US 2015/0009311 A1    Jan. 8, 2015

Related U.S. Application Data

(62) Division of application No. 13/247,613, filed on Sep. 28, 2011, now Pat. No. 8,870,751.

(30) Foreign Application Priority Data

Sep. 28, 2010 (JP) .................................. 2010-217962
Sep. 28, 2010 (JP) .................................. 2010-217964

(51) Int. Cl.
*A61B 1/00* (2006.01)
*A61B 1/04* (2006.01)
(Continued)

(52) U.S. Cl.
CPC ......... *A61B 1/00009* (2013.01); *A61B 1/0002* (2013.01); *A61B 1/00055* (2013.01);
(Continued)

(58) Field of Classification Search
CPC .............. A61B 1/00009; A61B 1/0002; A61B 1/00055; A61B 1/05; A61B 1/273; A61B 6/563; A61B 34/10; G06T 7/0012; G06T 2207/10016; G06T 2207/30004; G06T 2210/41; G06T 7/408; G06T 2200/24; G06T 7/001; G06T 7/0024; G06T 2207/10068; G06T 7/0014; G06T 7/0028; G06T 7/0081; G06T 7/2053; G06F 19/321; G06F 17/30247; G06F 19/3443; G06Q 50/22; G06Q 30/0267; G06Q 30/0255
(Continued)

(56) References Cited

U.S. PATENT DOCUMENTS 4,312,581 A    1/1982    Miyagawa et al.
5,081,483 A    1/1992    Ishimura et al.
(Continued)

FOREIGN PATENT DOCUMENTS

JP    03-122608    5/1991
JP    2000-081303   3/2000
(Continued)

OTHER PUBLICATIONS

Office Action issued on Oct. 22, 2013 in the corresponding Japanese Patent Application (JP-OA-2010-217962) with partial English translation.

*Primary Examiner* — John P Leubecker
*Assistant Examiner* — Arnaldo Torres Diaz
(74) *Attorney, Agent, or Firm* — Young & Thompson

(57) ABSTRACT

Plural predetermined examination parts of a patient are imaged sequentially and still images of the respective examination parts are thereby acquired by inserting an endoscope insertion unit having an imaging optical system in its tip portion into the body cavity of the patient. To this end, the number of still images taken is counted every time one of the predetermined examination parts. The counted (Continued)

number of still images taken is compared with a preset number of images which corresponds to the number of the plural predetermined examination parts. An alert is generated when non-coincidence is detected between the counted number of still images taken and the preset number. The operator is thus notified of occurrence of a failure to image.

10 Claims, 21 Drawing Sheets

(51) Int. Cl.
    *A61B 1/045* (2006.01)
    *A61B 1/05* (2006.01)
    *A61B 1/273* (2006.01)

(52) U.S. Cl.
    CPC ............... *A61B 1/045* (2013.01); *A61B 1/05* (2013.01); *A61B 1/273* (2013.01)

(58) Field of Classification Search
    USPC ............................................ 600/117; 348/74
    See application file for complete search history.

(56) References Cited

U.S. PATENT DOCUMENTS

| | | | |
|---|---|---|---|
| 5,564,012 A * | 10/1996 | Shigyo | G06F 11/22 714/15 |
| 5,651,362 A * | 7/1997 | Shigyo | G06F 11/22 250/580 |
| 5,655,162 A | 8/1997 | Nakamura et al. | |
| 5,668,897 A * | 9/1997 | Stolfo | G06F 17/30247 382/283 |
| 5,729,775 A | 3/1998 | Ohta et al. | |
| 6,028,910 A | 2/2000 | Kirchner et al. | |
| 6,510,287 B1 | 1/2003 | Tsukahara et al. | |
| 7,800,679 B2 | 9/2010 | Wakabayashi | |
| 8,194,096 B2 | 6/2012 | Hirakawa et al. | |
| 8,353,816 B2 * | 1/2013 | Shimizu | A61B 1/00009 348/65 |
| 8,782,506 B2 * | 7/2014 | Yamaji | G06T 11/60 715/202 |
| 2005/0063565 A1 | 3/2005 | Nagaoka et al. | |
| 2006/0171603 A1 | 8/2006 | Jung et al. | |
| 2006/0171695 A1 | 8/2006 | Jung et al. | |
| 2006/0174204 A1 | 8/2006 | Jung et al. | |
| 2006/0174205 A1 | 8/2006 | Jung et al. | |
| 2006/0174206 A1 | 8/2006 | Jung et al. | |
| 2007/0035635 A1 * | 2/2007 | Misawa | H04N 5/23245 348/222.1 |
| 2007/0236505 A1 | 10/2007 | Jung et al. | |
| 2008/0106621 A1 | 5/2008 | Jung et al. | |
| 2008/0112644 A1 | 5/2008 | Yokohata et al. | |
| 2008/0158366 A1 | 7/2008 | Jung et al. | |
| 2008/0219589 A1 | 9/2008 | Jung et al. | |
| 2008/0240497 A1 | 10/2008 | Porikli et al. | |
| 2008/0242926 A1 | 10/2008 | Nishino | |
| 2009/0043157 A1 | 2/2009 | Hirakawa et al. | |
| 2009/0147100 A1 | 6/2009 | Nagamasa et al. | |
| 2009/0203964 A1 | 8/2009 | Shimizu et al. | |
| 2009/0227837 A1 * | 9/2009 | Shimizu | A61B 1/00009 600/109 |
| 2009/0240108 A1 * | 9/2009 | Shimizu | A61B 1/041 600/109 |
| 2009/0249177 A1 | 10/2009 | Yamaji et al. | |
| 2009/0252390 A1 | 10/2009 | Matsuzaki et al. | |
| 2010/0013757 A1 | 1/2010 | Ogikubo | |
| 2010/0023556 A1 * | 1/2010 | Sawada | A61B 6/037 707/E17.009 |
| 2010/0023961 A1 | 1/2010 | Kim | |
| 2010/0040344 A1 | 2/2010 | Mizuno et al. | |
| 2010/0115036 A1 | 5/2010 | Rosner et al. | |
| 2010/0261960 A1 | 10/2010 | Miyahara | |
| 2012/0078046 A1 * | 3/2012 | Sasaki | A61B 1/00009 600/109 |
| 2015/0009311 A1 * | 1/2015 | Sasaki | A61B 1/00055 348/74 |

FOREIGN PATENT DOCUMENTS

| | | |
|---|---|---|
| JP | 2000-135215 | 5/2000 |
| JP | 2004-356797 | 12/2004 |

\* cited by examiner

SENSOR OUTPUT

ENDOSCOPE IMAGE RECORDING APPARATUS, ENDOSCOPE IMAGE ACQUISITION ASSISTING METHOD AND COMPUTER READABLE MEDIUM

CROSS-REFERENCE TO RELATED APPLICATIONS

This application claims the benefit of Japanese Patent Application Nos. 2010-217962 filed on Sep. 28, 2010, and 2010-217964 filed on Sep. 28, 2010, the entire contents of which are hereby incorporated by reference, the same as if set forth at length; the entire of which are incorporated herein by reference.

BACKGROUND OF THE INVENTION

1. Technical Field

The present invention relates to an endoscope system, an endoscope image recording apparatus, an endoscope image acquisition assisting method, and a related computer readable medium.

2. Description of Related Art

In an endoscopic examination, plural parts to be examined are determined in advance and a diagnosis is made based on images taken by imaging the inside of the body cavity of a patient by a prescribed procedure. An operator is required to perform imaging work fast and accurately because several to more than 20 images are taken per examination and it is desired in hospitals etc. to examine a number of patients in a short time. In such a situation, a mistake tends to occur such as a failure to image some parts to be examined. A failure to image some parts makes it difficult to make a correct diagnosis, and re-imaging is a heavy load on the patient.

Additionally, in endoscopic examinations, one or plural parts to be examined in the body cavity are determined in advance for each patient (subject person) and a diagnosis is made based on images taken by imaging those examination parts by a prescribed procedure. More specifically, the operator of an endoscope inserts the insertion unit of the endoscope into the body cavity of a patient and advances the tip portion of the insertion unit of the endoscope to each predetermined examination part while checking the position of the tip portion of the insertion unit in the body cavity. Every time the tip portion of the insertion unit reaches an examination part, the operator takes a still image by pushing a still image imaging button while checking a image displayed on a monitor screen and fine-adjusting the imaging position and direction.

Operators are required to perform imaging work fast and accurately because several to more than 20 images are taken per examination and it is desired in hospitals etc. to examine a number of patients in a short time. In such a situation, a mistake tends to occur such as a failure to image some parts to be examined. A failure to image some parts makes it difficult to make a correct diagnosis, and re-imaging to acquire missing images is a heavy load on the patient.

Various apparatus for detecting the position of the insertion unit of an endoscope in a body cavity have been developed as parts of techniques for guiding the insertion unit to a desired examination part. For example, in a position detecting apparatus of JP-A-2000-081303, the insertion unit of an endoscope is provided with magnetism generating units and an examination bed is provided with magnetic sensors. The position of insertion unit of the endoscope in a body cavity is detected from results of detection of the magnetism generating unit by the magnetic sensors.

JP-A-2000-135215 proposes an endoscope insertion assisting apparatus which generates a 3D image of a tubular passage of a subject based on 3D image data of the subject, generates, in the generated 3D image, a virtual endoscope image of a route to a destination along the tubular passage based on image data, and displays the generated virtual endoscope image. This endoscope insertion assisting apparatus makes it possible to move the insertion unit of the endoscope to a desired position reliably.

SUMMARY

However, in endoscopic examinations, there may occur an event that the number of still images taken is smaller than an intended number due to, for example, an incomplete manipulation of a still image shooting button, an erroneously recognized manipulation by an operator, or a misjudgment of an operator. As a result, a part that the operator thinks has just been shot may not be a part that has been shot actually.

In view of the above, it is considered to establish an accurate imaging by understanding examination parts by means of the apparatus of JP-A-2000-081303 or JP-A-2000-135215. However, the position detecting apparatus of JP-A-2000-081303 is of a large scale because magnetism generating means and the magnetic sensors need to be provided on the examination bed or the like so as to correspond to the entire body of a patient. In the endoscope insertion assisting apparatus of JP-A-2000-135215, it is necessary to generate 3D image data in advance by means of a CT apparatus. As such, either apparatus cannot be used in a simple manner.

An object of the present invention is to provide an endoscope system, an endoscope image acquisition assisting method, and a program which make it possible to acquire pieces of image information of desired examination parts by imaging predetermined examination parts simply and reliably (i.e., without failing to image some of them) without the need for using a large-scale apparatus or making a lot of preparations.

Additionally, an object of the present invention is to provide an endoscope image recording apparatus, an endoscope image recording assisting method, and a program which can assist work of generating missing still images based on moving image data to complete still image data when a shortage in the number of still images of examination parts is found even after completion of an endoscopic examination in which parts that need to be examined are specified in advance.

The invention is constituted as below.

(1) An endoscope system sequentially images plural predetermined examination parts of a patient and thereby acquires still images of the respective examination parts by inserting an endoscope insertion unit having an imaging optical system in its tip portion into a body cavity of the patient. The endoscope system includes a number-of-images counting unit, a number-of-images comparing unit and an alert generating unit. The number-of-images counting unit counts the number of still images taken every time one of the predetermined examination parts is imaged. The number-of-images comparing unit compares the counted number of still images with a preset number of images which corresponds to the number of the plural predetermined examination parts. The alert generating unit generates an alert when the number-of-images comparing unit detects non-coincidence between the counted number of still images taken and the preset number.

(2) An endoscope image acquisition assisting method sequentially images plural predetermined examination parts of a patient and thereby acquires still images of the respective examination parts by inserting an endoscope insertion unit having an imaging optical system in its tip portion into a body cavity of the patient. The endoscope image acquisition assisting method includes: counting the number of still images taken every time one of the predetermined examination parts is imaged; comparing the counted number of still images with a preset number of images which corresponds to the number of the plural predetermined examination parts; and generating an alert when non-coincidence is detected between the counted number of still images taken and the preset number.

(3) A non-transitory computer readable medium causes a computer to execute a process of the endoscope image acquisition assisting method according to (2).

(4) An endoscope image recording apparatus records examination image data including data of still images of a preset, plural number of examination parts based on an image signal which is output from an endoscope when a patient is subjected to an endoscopic examination. The endoscope image recording apparatus includes a data storage unit, a number-of-recorded-images detecting unit, a number-of-images comparing and judging unit and a signal output unit. The data storage unit stores, based on the image data, moving image data representing a moving image and still image data representing still images each of which is imaged upon reception of a prescribed instruction. The number-of-recorded-images detecting unit detects the number of recorded still images from the still image data stored in the data storage unit. The number-of-images comparing and judging unit compares the number of recorded still images detected by the number-of-recorded-images detecting unit with a total number of images which corresponds to the plural examination parts, and judges whether or not the number of recorded still images is smaller than the total number of images. The signal output unit outputs an image acquisition assist signal for acquisition of a missing still image from the moving image data stored in the data storage unit when the number-of-images comparing and judging unit judges that the number of recorded still images is smaller than the total number of images.

(5) An endoscope image recording assisting method records examination image data including data of still images of a preset, plural number of examination parts based on an image signal which is output from an endoscope when a patient is subjected to an endoscopic examination. The endoscope image recording assisting method includes: detecting the number of recorded still images from the stored still image data after both of moving image data representing a moving image and still image data representing still images each of which is imaged upon reception of a prescribed instruction are stored based on the image signal; comparing the detected number of recorded still images with a total number of images which corresponds to the plural examination parts; and outputting an image acquisition assist signal for acquisition of a missing still image from the stored moving image data when the number of recorded still images is judged smaller than the total number of images.

(6) A non-transitory computer readable medium causes a computer to execute a process of the endoscope image recording assisting method according to (5).

The invention makes it possible to acquire pieces of image information of desired examination parts by imaging predetermined examination parts simply and reliably (i.e., without failing to image some of them) without the need for using a large-scale apparatus or making a lot of preparations. The invention thus makes it possible to perform an endoscopic examination correctly and rapidly.

Additionally, the invention can assist work of generating missing still images based on moving image data to complete still image data when a shortage in the number of still images of examination parts is found even after completion of an endoscopic examination in which parts that need to be examined are specified in advance. Since still images of all examination parts are always acquired reliably, the accuracy of diagnosis is not lowered and the load on a patient can be reduced. For example, an endoscopic re-examination for imaging missing images can be avoided.

DETAILED DESCRIPTION OF EMBODIMENTS OF THE INVENTION

Embodiments of the present invention will be hereinafter described in detail with reference to the drawings.

Figure 1:
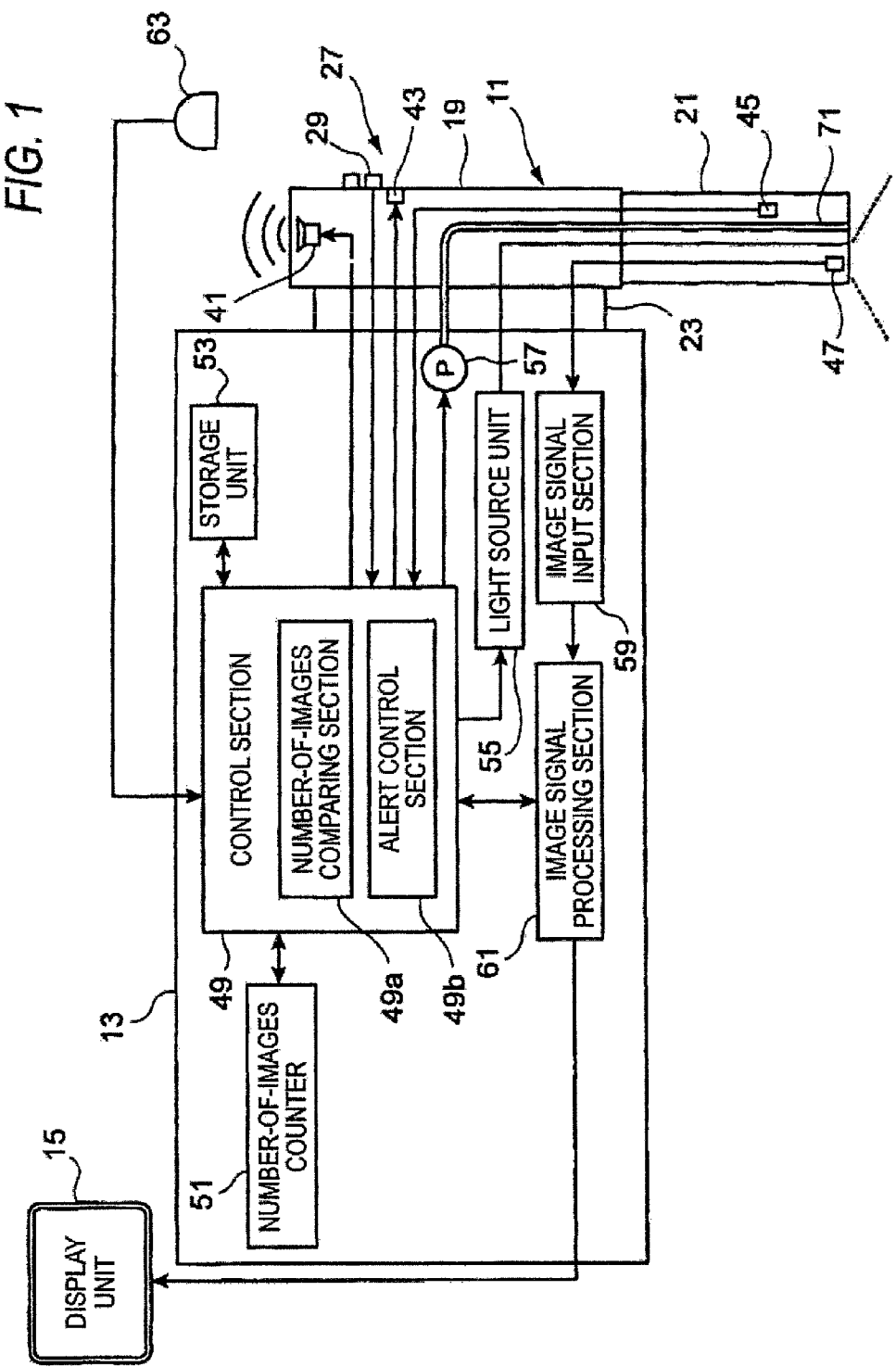
FIG. 1 is a block diagram showing the configuration of an endoscope system according to a first embodiment of the present invention.
Figure 2:
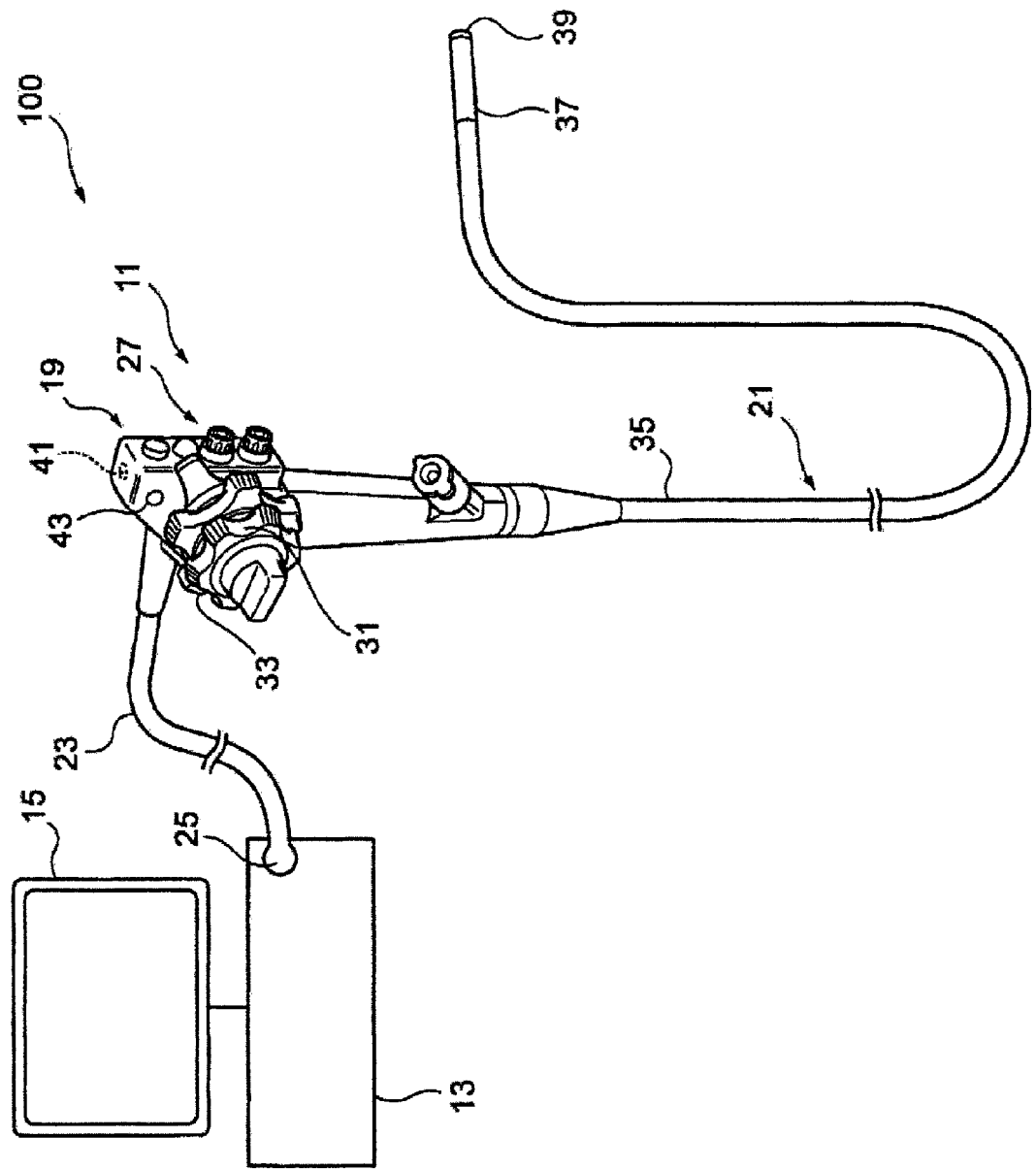
FIG. 2 shows the configuration of the entire endoscope system.

FIG. 1 is a block diagram showing the configuration of an endoscope system according to a first embodiment of the invention. FIG. 2 shows the configuration of the entire endoscope system.

In the endoscope system 100 according to the first embodiment, an insertion unit of an endoscope is inserted into the body cavity of a patient, predetermined examination parts are imaged, and imaged images of the examination parts are recorded. The endoscope system 100 has a function of checking the number of still images that have been taken until the end of an examination and, if the number of images is smaller than a predetermined number, generating an alert to urge the endoscope operator to do re-imaging in, for example, an endoscopic examination in which observation subjects are determined in advance.

As shown in FIG. 1, the endoscope system 100 is equipped with an endoscope 11 having an imaging optical system and an illumination optical system, an endoscope control apparatus 13 as a control means (described later) for controlling the endoscope 11, and a display unit 15 for displaying image information etc. Although not shown in FIG. 1, the endoscope control apparatus 13 is connected to a server via a network and hence can receive and output various kinds of information.

As shown in FIG. 2, the endoscope 11 is equipped with a main body manipulation unit 19 and an endoscope insertion unit 21 which is continuous with the main body manipulation unit 19 and is to be inserted into a body cavity. One end of a universal cord 23 is connected to the main body manipulation unit 19, and the other end of it is connected to the endoscope control apparatus 13 by a light guide connector 25.

Various manipulation buttons 27 such as buttons for performing suction, air feed, and water feed at the tip (located on the side that is more distant from the main body manipulation unit 19) of the endoscope insertion unit 21 and a shutter button for imaging are arranged on the main body manipulation unit 19 of the endoscope 11, and a pair of angle knobs 31 and 33 are attached to the main body manipulation unit 19.

The endoscope insertion unit 21 is composed of a soft portion 35, a curved portion 37, and a tip portion (hereinafter referred to as an endoscope tip portion) 39. A curving manipulation can be performed on the curved portion 37 remotely by rotating the angle knobs 31 and 33 of the main body manipulation unit 19, whereby the endoscope tip portion 39 can be directed to a desired direction.

Figure 3:
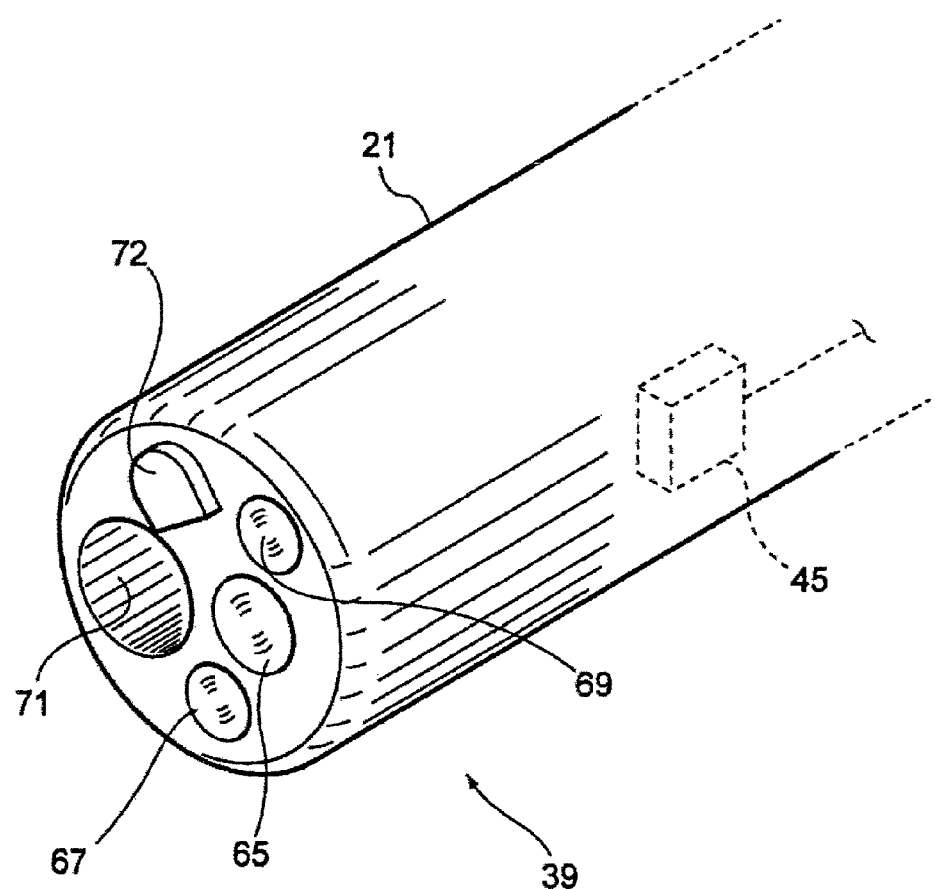
FIG. 3 is a perspective view of an endoscope tip portion.

FIG. 3 is a perspective view of the endoscope tip portion 39. The endoscope tip portion 39 is provided with an observation window 65 of the imaging optical system, light emission windows 67 and 69 of the illumination optical system, a forceps hole 71, and an air feed/water feed nozzle 72. The imaging optical system is configured so as to image reflection light from an observation subject region (in a body cavity) being illuminated with illumination light beams that are emitted from the light emission windows 67 and 69. An observation image thus taken is sent to the endoscope control apparatus 13 via the universal cord 23 (see FIG. 2). The endoscope control apparatus 13 performs proper image processing on the imaged image and displays a resulting image on the display unit 15.

Being an imaging unit having an imaging device 47 such as a CCD (charge-coupled device) or a CMOS (complementary meta-oxide-semiconductor) sensor and optical members such as an image-forming lens disposed in front of the imaging device 47 on its optical path, the imaging optical system acquires an observation image through the observation window 65 and outputs a resulting imaging signal to the endoscope control apparatus 13.

The illumination optical system guides, to the endoscope tip portion 39, illumination light that is transmitted from the endoscope control apparatus 13 via the universal cord 23, and emits resulting light beams to an observation subject region through the light emission windows 67 and 69.

Various operation tools (not shown) are inserted through the forceps hole 71 (see FIG. 3). Connected to a pump 57 (see FIG. 1), the forceps hole 71 can serve for suction. The air feed/water feed nozzle 72 can send out air or water toward the observation window 65.

The basic configuration of the endoscope 11 has been described above. In addition, the main body manipulation unit 19 is equipped with a hand manipulation end button 29 for notification of the end of a series of hand manipulations and a speaker 41 and a light-emitting unit 43 for notifying an operator. An acceleration sensor 45 for detecting a variation of a moving speed of the endoscope insertion unit 21 is disposed at the tip of the endoscope insertion unit 21.

The endoscope control apparatus 13 is equipped with a number-of-images counter 51 for counting the number of still images taken, a storage unit 53, a light source unit 55 for supplying illumination light to the illumination optical system, the pump 57 for performing suction through the forceps hole 71 and air feed through the air feed/water feed nozzle 72, an image signal input section 59 for receiving an image signal from the imaging device of the endoscope 11, and an image signal processing section 61 for performing computation on the received image signal. A microphone 63 which is disposed in the vicinity of the endoscope 11 is connected to a control section 49.

The number-of-images counter 51 functions as a number-of-imaged-images counting means which counts the number of still images taken and supplies the control section 49 with information of the number of images taken so far.

The storage unit 53 functions as an examination position information storage means for storing examination position information indicating positions, in a body cavity, of predetermined examination parts and patient information such as a height, a weight, an age, and a medical history of a patient. The storage unit 53 outputs various kinds of information in response to an inquiry from the control section 49.

The light source unit 55 is a white light source such as a xenon lamp, a halogen lamp, or a metal halide lamp. Alternatively, the light source unit 55 may be a laser light source or a light source using a semiconductor light-emitting device such as a light-emitting diode.

The control section 49 controls the individual units connected to it, and receives an output signal from the numberof-images counter 51 every time an examination part is imaged. The control section 49 is equipped with a number-of-images comparing section 49a for comparing a counted number of images taken with a preset number of images to be taken that corresponds to the number of plural predetermined examination parts and an alert control section 49b for generating an alert upon detection of non-coincidence between the number of images taken and the preset number. The number-of-images comparing section 49a and the alert control section 49b will be described later in detail.

Next, using an example endoscopic examination, a description will be made of how the above-configured endoscope system 100 operates when an endoscopic examination is performed.

Figure 4:
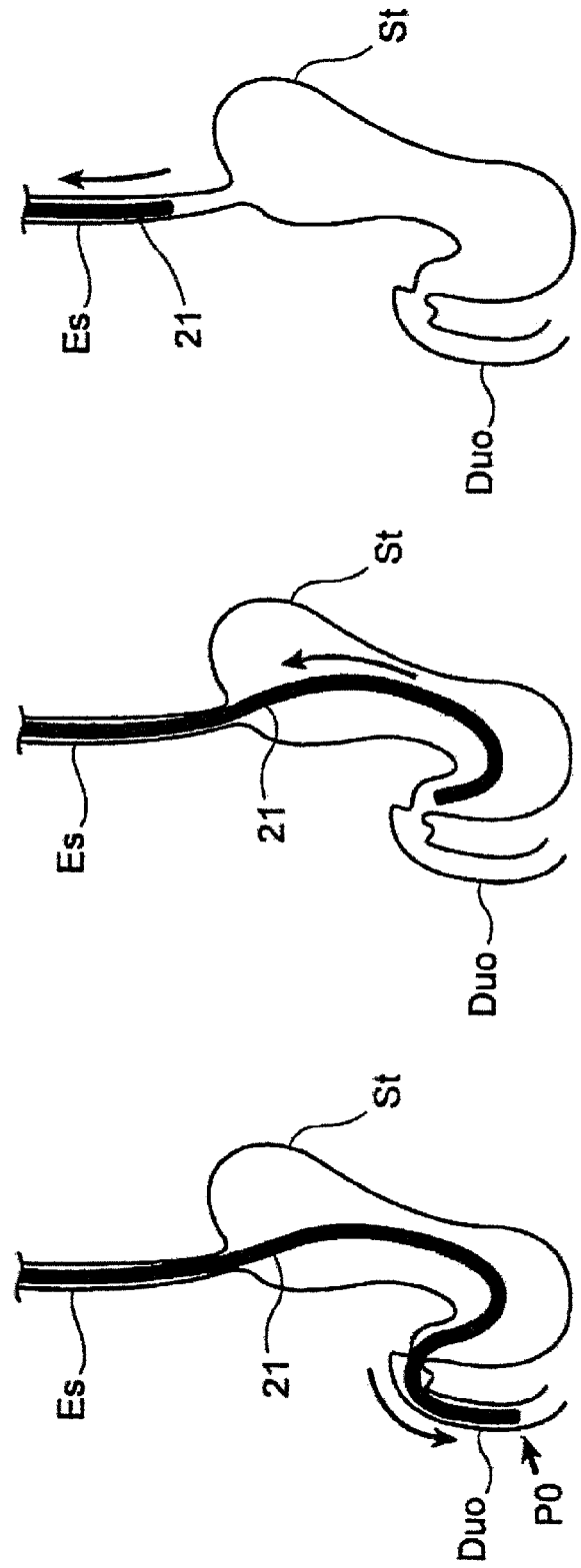
FIG. 4A illustrates a state that an endoscope insertion unit has been inserted through the esophagus and the stomach to an examination deepest position in the duodenum.
FIG. 4B illustrates how the stomach region is imaged.
FIG. 4C illustrates how the esophagus region is imaged.

FIGS. 4A-4C illustrate a procedure of an endoscopic examination of the upper digestive tract. In this example endoscopic examination of the upper digestive tract, first, as shown in FIG. 4A, the endoscope insertion unit 21 is inserted through the esophagus Es and the stomach St to an examination deepest position P0 in the duodenum Duo. When the endoscope insertion unit 21 has reached the examination deepest position P0, the operator takes a still image (observation image) there. Then, the operator moves the endoscope insertion unit 21 through the body cavity while pulling it gradually. In doing so, the operator images the region of the stomach St (see FIG. 4B) and the region of the esophagus Es (see FIG. 4C) in order. Finally, the operator removes the endoscope insertion unit 21 from the body cavity.

Figure 5:
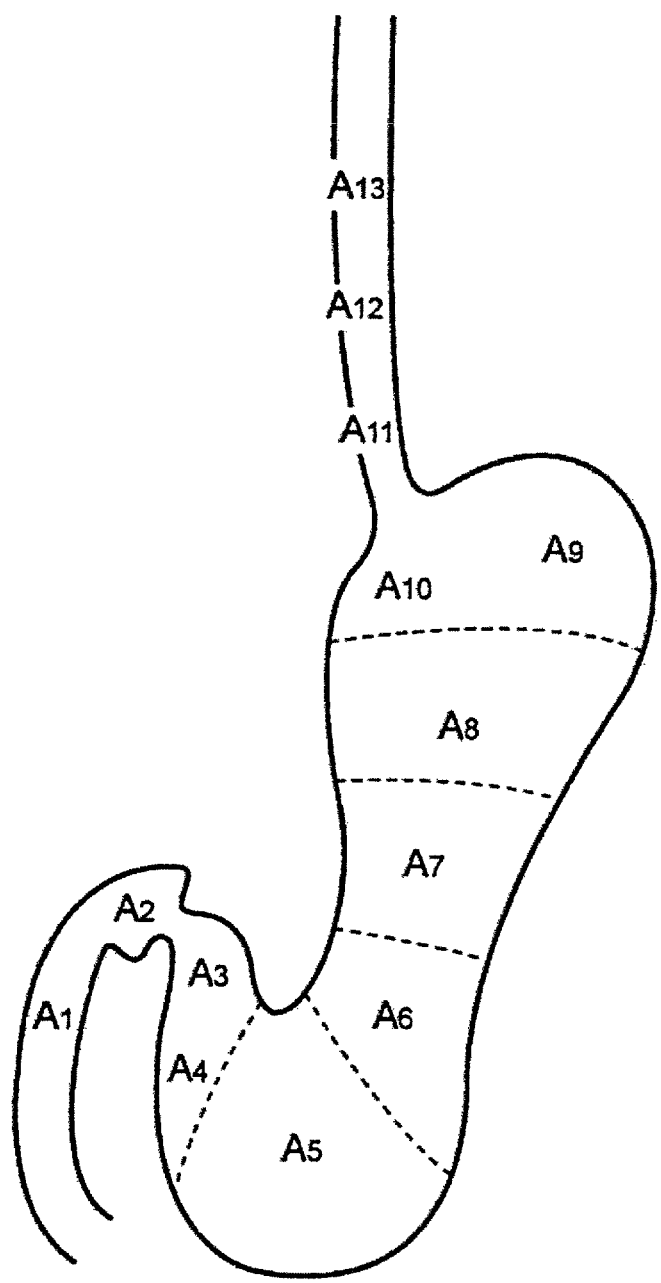
FIG. 5 shows specific examination parts of an endoscopic examination.

FIG. 5 shows specific examination parts of the endoscopic examination to be performed by the above procedure. The endoscopic examination parts are divisional regions A1-A13, arranged in this order from the examination deepest position P0, of the duodenum Duo, stomach St, and esophagus Es.

TABLE 1

| Region | Name of examination part | Position in body cavity |
| --- | --- | --- |
| A1 | Postbulbus of duodenum and lower part | P0-P1 |
| A2 | Duodenal bulb | P1-P2 |
| A3 | Pylorus front part | P2-P3 |
| A4 | Pylorus anterior wall | P3-P4 |
| A5 | Angular incisure | P4-P5 |
| A6 | Lower part of stomach body | P5-P6 |
| A7 | Middle part of stomach body | P6-P7 |
| A8 | Upper part of stomach body | P7-P8 |
| A9 | Fundus ventriculi (posterior wall of gastic fundus) | P8-P9 |
| A10 | Cardiac region of stomach | P9-P10 |
| A11 | Lower part of esophagus | P10-P11 |
| A12 | Middle part of esophagus | P11-P12 |
| A13 | Upper part of esophagus | P12-P13 |

The operator of the endoscope 11 moves the endoscope tip portion 39 to the individual examination parts and takes still images at the respective positions. The still images of the respective examination parts are stored in the endoscope control apparatus 13 together with the patient information, and the operator writes a report of the endoscopic examination based on the recorded information.

Figure 6:
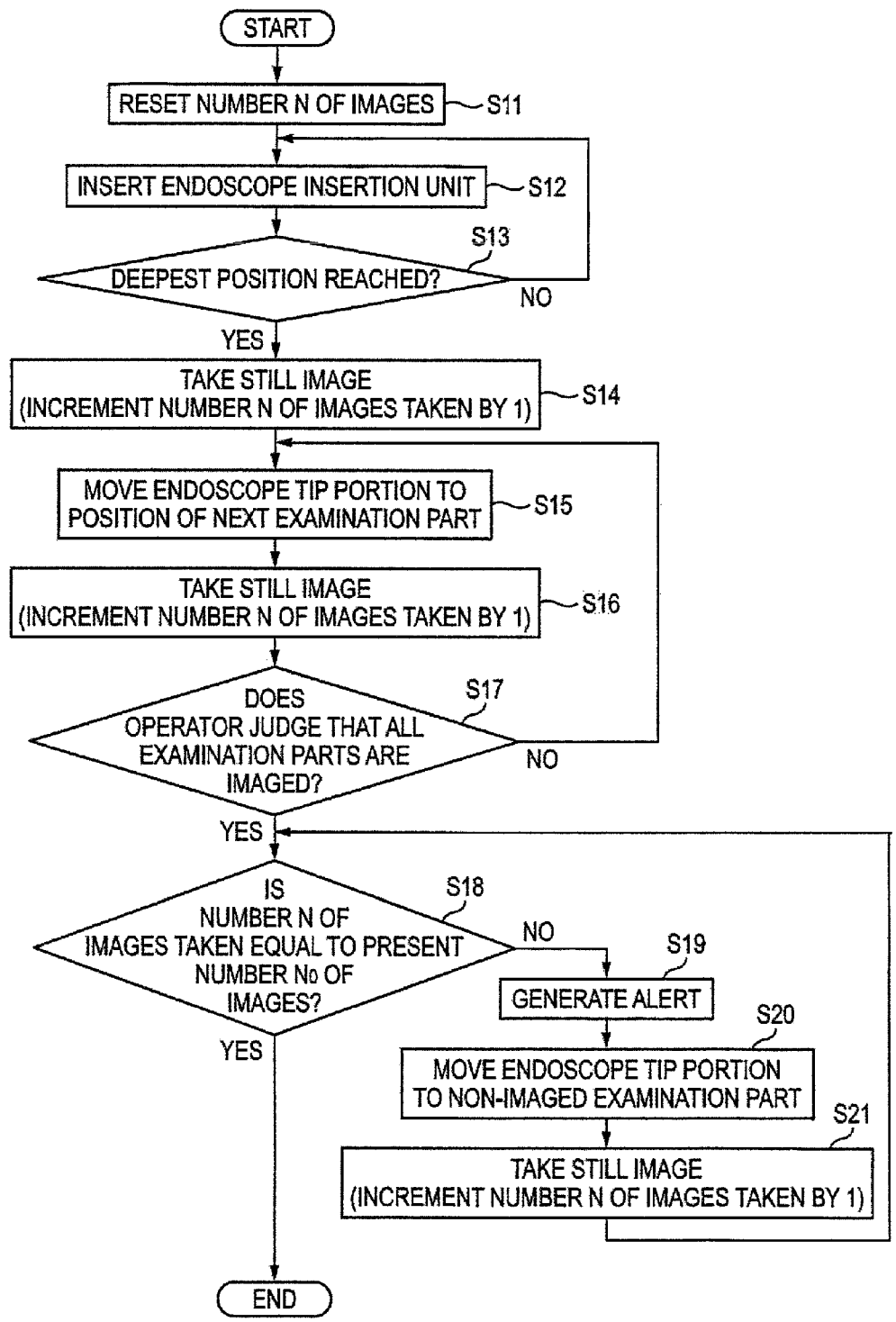
FIG. 6 is a flowchart of an endoscopic examination procedure.

FIG. 6 is a flowchart of an endoscopic examination procedure. A procedure for performing an endoscopic examination on examination parts shown in Table 1 will be described with reference to FIG. 6.

First, after prescribed pre-examination treatment has been given to a patient, at step S11 the control section 49 resets the count of the number-of-images counter 51. At step S12, the operator of the endoscope 11 inserts the endoscope insertion unit 21 into the body cavity. The operator advances the endoscope insertion unit 21 until the endoscope tip portion 39 reaches the examination deepest position P0 (the postbulbus of the duodenum or lower) of the body cavity of the patient while checking observation images that are output from the endoscope 11 and displayed on the display unit 15 (step S13).

After the endoscope tip portion 39 reached the examination deepest position P0, the operator pushes the shutter button which is one of the manipulation buttons 27 of the main body manipulation unit 19 of the endoscope 11. A resulting shutter button pushing signal is sent to the endoscope control apparatus 13 as a first imaging instruction signal.

In response to the first imaging instruction, at step S14 the endoscope control apparatus 13 takes a still image at the examination part in region A1 of the body cavity. Since this is the first still image taking, the number-of-images counter 51 automatically changes its count to "1." After the end of the still image taking at region A1, at step S15 the operator moves the endoscope tip portion 39 to the next region A2. When still image taking has been performed at region A2, at step S16 the count of the number-of-images counter 51 is incremented to "2."

Steps S15 and S16 are executed for all the examination parts excluding the first one. During that course, as shown in FIG. 7, an observation image 73 and interim information 74 including the number of images taken so far and the number of all examination parts are displayed on the display unit 15.

Figure 7:
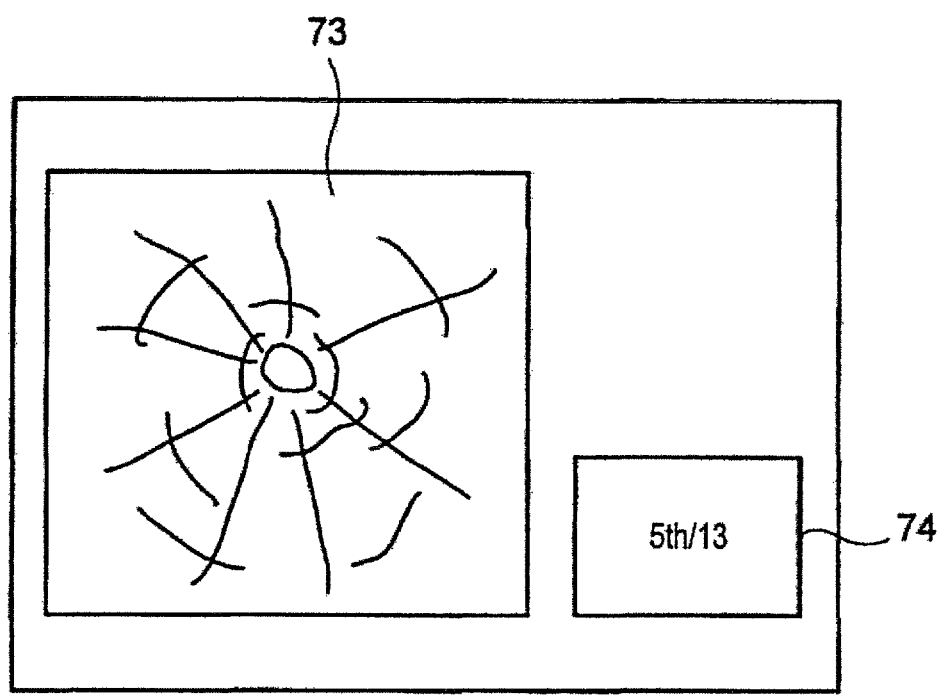
FIG. 7 shows an example picture displayed on a display unit.

Since the number of still images taken, that is, the count of the number-of-images counter 51, and a preset number of images to be taken that corresponds to the number of predetermined examination parts are displayed as shown in FIG. 7, the operator can easily recognize where the current examination part stands in the order of the examination parts.

If judging that still image taking has been performed for all the examination parts (S17: yes), the operator pushes the hand manipulation end button 29. A resulting signal is input to the control section 49, and at step S18 the control section 49 judges whether or not the number N of still images taken is equal to the preset number $N_0$ of images using the number-of-images comparing section 49a.

If the number-of-images comparing section 49a detects non-coincidence between the number N of still images taken and the preset number $N_0$ of images (S18: no), at step S19 the alert control section 49b outputs an alert signal to the speaker 41 provided on the endoscope 11 and thereby causes the speaker 41 to generate an alert such as an alarm sound or a voice to notify the operator of the non-coincidence. In this manner, the operator is notified of the fact that the number N of still images taken has not reached the preset number $N_0$ (in this example, 13) of images yet. Generating an alert in the form of a sound or a voice makes it possible to notify not only the operator but also persons around the operator who are also performing hand manipulations.

When an alert is generated, at step S20 the operator determines an examination part for which he or she failed to take a still image by manipulating the endoscope control apparatus 13 and moves the endoscope tip portion 39 there. At step S21, the operator takes a still image and the control section 49 causes the number-of-images counter 51 to increment the number N of still images taken by 1. The process returns to step S18, where the control section 49 judges whether or not the number N of still images taken has reached the preset number $N_0$ of images using the number-of-images comparing section 49a.

If the number N of still images taken has reached the preset number $N_0$ of images (S18: yes), the operator removes the endoscope insertion unit 21 completely from the body cavity and finishes the examination.

As described above, the endoscope system 100 according to the embodiment makes it possible to acquire pieces of image information of all desired examination parts by imaging predetermined examination parts simply and reliably (i.e., without failing to image some of them) without the need for using a large-scale apparatus or making a lot of preparations. In the event of a shortage in the number of images taken, an alert is generated before the end of an endoscopic examination to urge the operator to perform re-imaging. This allows the operator to avoid re-inserting the endoscope insertion unit 21 into the body cavity of a patient after removing it. The load on the patient can thus be reduced.

Whether or not the operator has judged that still image taking has been performed on all the examination parts (step S17) can be judged in the following manner instead of detecting pushing of the hand manipulation end button 29 by the operator.

(a) If a variation of the movement speed of the endoscope tip portion 39 detected by the acceleration sensor 45 is faster than a threshold value, it is judged that the operator is removing the endoscope insertion unit 21 from the esophagus, that is, the operator is making an action for finishing the examination.

(b) If a voice "Finished" or the like of the operator, for example, is picked up by the microphone 63, it is judged that the operator has judged that the examination should be finished. This is enabled by voice-recognizing a particular word(s) by analyzing an audio signal supplied from the microphone 69 by means of a voice recognition means provided in the control section 49.

(c) The hue of observation images that are output from the imaging device 47 of the endoscope 11 are analyzed sequentially by the image signal processing section 61. If the hue of the entire image has changed, it is judged that the operator has judged that the examination should be finished. The duodenum, the stomach (reddish), and the esophagus (whitish) are different from each other in hue. If the hue of the image taken is changed from reddish to whitish, it is judged that the endoscope tip portion 39 is passing through the esophagus, that is, the operator is finishing the examination.

(d) If an air suction operation is performed by means of the pump 57, it is judged that the operator has judged that the examination should be finished. After parts of an organ are imaged by expanding it by feeding air into it through the endoscope 11, the air in the organ may be sucked out. Thus, if such an air suction operation for air ejection is detected, it is judged that the operator has judged that the examination should be finished.

Whether or not the operator has judged that the examination should be finished may be judged by any of the above methods or a combination thereof.

The alert generating means is not limited to the above-described means of notification using the speaker 41. Other examples are displaying alert information on the display unit 15, lighting the light-emitting unit 43 of the main body manipulation unit 19 or a light-emitting device such as an alarm lamp (not shown) provide inside or outside the endoscope control apparatus 13, and vibrating a vibrator (not shown) that is built in the main body manipulation unit 19. Employing a visual or tactile alert makes it possible to notify only the operator without causing a patient to feel anxious unnecessarily by sensing an alert.

Figure 8:
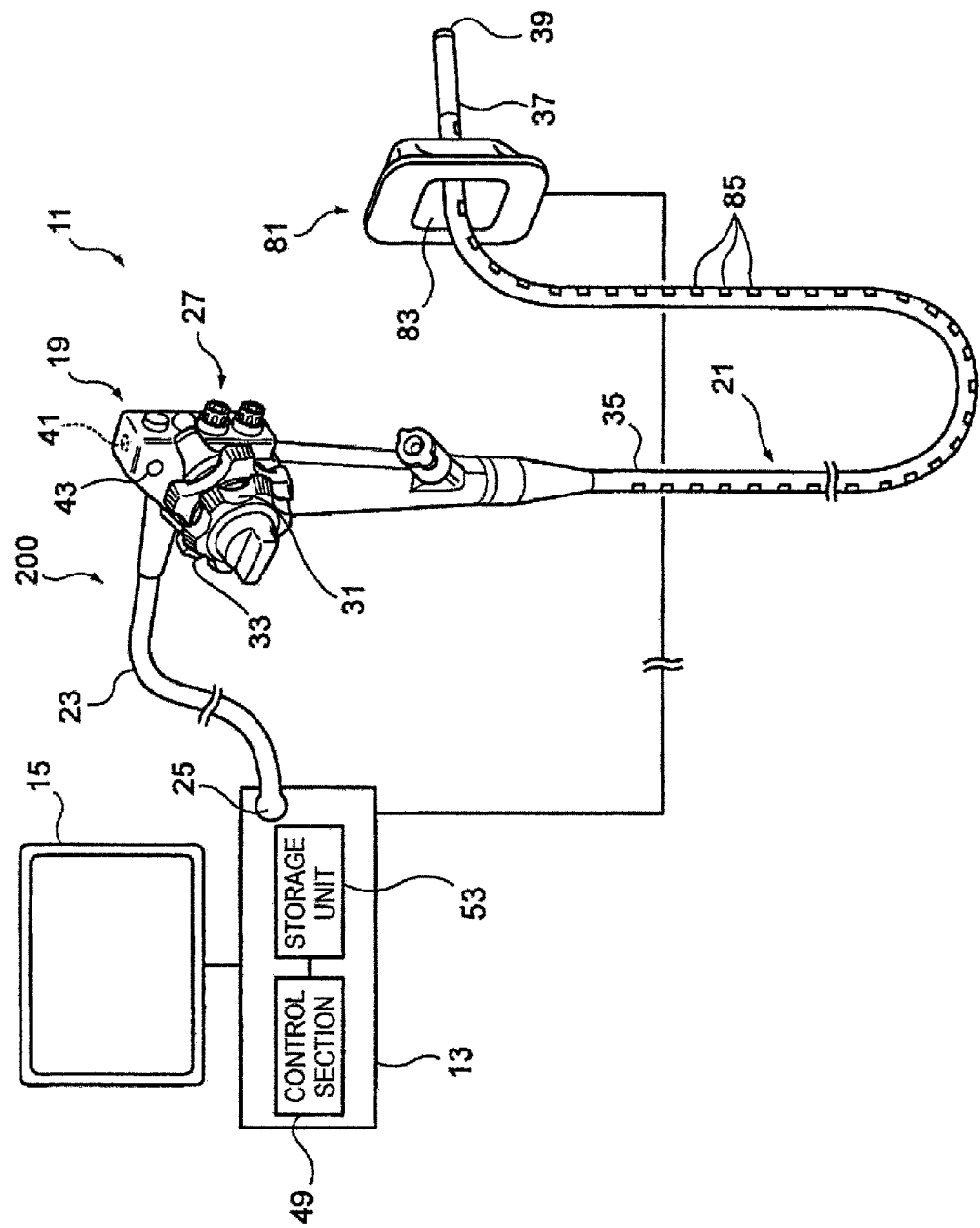
FIG. 8 shows the configuration of the entire endoscope system according to a second embodiment.

Next, an endoscope system according to a second embodiment will be described. FIG. 8 shows the configuration of the entire endoscope system according to the second embodiment.

In the endoscope system 200, after the endoscope insertion unit is inserted into the body cavity of a patient, predetermined examination parts are imaged and imaged images of the respective examination parts are recorded while the position of an endoscope tip portion in the body cavity is detected. During that course, the number of still images taken is checked. If a shortage occurs in the number of still images taken, an alert is generated and the operator is urged to perform re-imaging in the midst of the examination. That is, it is possible to generate an alert not only immediately before the end of an endoscopic examination but also in the midst of a series of examination hand manipulations.

In addition to an endoscope 11A having an imaging optical system and an illumination optical system, an endoscope control apparatus 13 as a imaging control means (described later) for controlling the endoscope 11A, and a display unit 15 for displaying image information, the endoscope system 200 is equipped with a mouthpiece 81 as an insertion unit guide tool and an endoscope insertion unit 21A which enables detection of positions of the endoscope tip portion 39 relative to the mouthpiece 81. In the following description, constituent elements having the same ones in FIG. 1 or 2 will be given the same reference symbols as the latter and their descriptions will be omitted or simplified.

Figure 9:
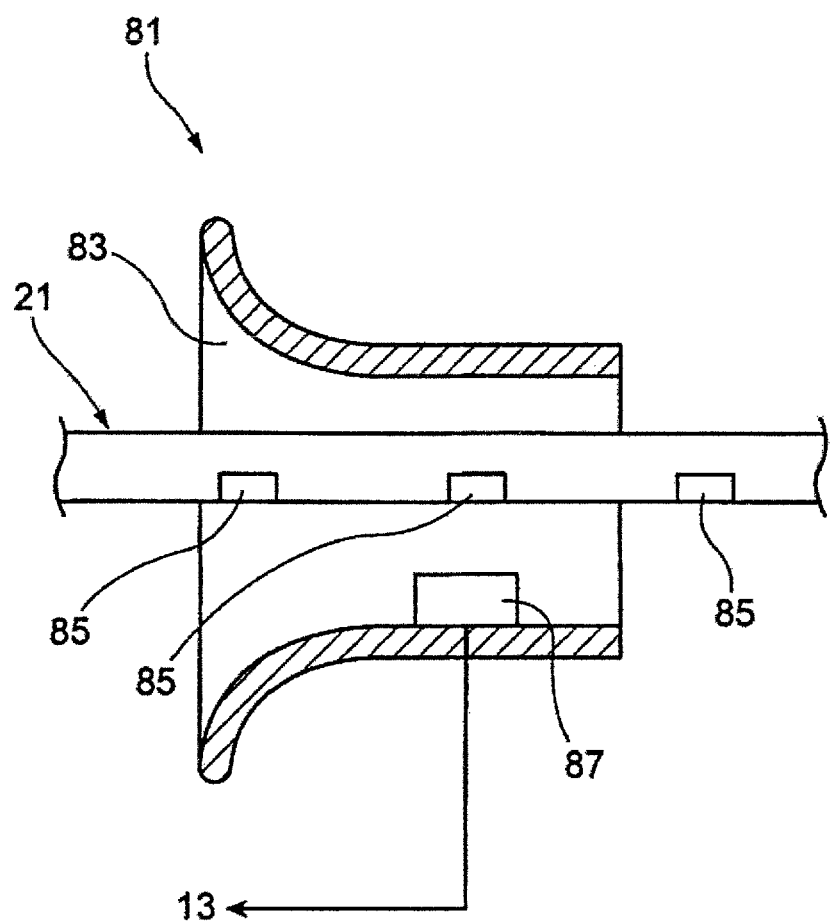
FIG. 9 is a sectional view of a mouthpiece in which an endoscope insertion unit is inserted.

FIG. 9 is a sectional view of the mouthpiece 81 in which the endoscope insertion unit 21A is inserted. The mouthpiece 81, which is to be attached to the opening of a body cavity (i.e., the mouth), has an insertion hole 83 into which the endoscope insertion unit 21A is to be inserted. Marking portions 85 which are magnetic media are arranged on the endoscope insertion unit 21A in the axial direction at regular intervals, and a marking reading unit 87 is provided on the inner surface of the insertion hole 83 of the mouthpiece 81 so as to be opposed to the marking portions 85. The marking reading unit 87 sends detection signals of read-out marking portions 85 to the endoscope control apparatus 13. The endoscope control apparatus 13 determines a length of insertion of the endoscope insertion unit 21A into the body cavity based on the number of pulses of the detection signals which represents the number of marking portions 85 detected. In this manner, the marking portions 85 and the marking reading unit 87 function as an endoscope tip position detecting means for detecting a length of insertion of the endoscope insertion unit 21A into a body cavity.

Being the combination of the magnetic media and the magnetic sensor, the endoscope tip position detecting means can detect position information accurately with high response speed. A position may be detected by reading pieces of optical information instead of pieces of magnetic information. For example, plural optical information bearing media having a different color than the surface color of the endoscope insertion unit 21A are arranged as marking portions on the endoscope insertion unit 21A in its longitudinal direction. The mouthpiece 81 is provided with an optical sensor for reading optical information from each marking portion by illuminating it with light and detecting reflection light. Thus, an insertion length of the endoscope insertion unit 21A can be detected with a simple configuration.

Figure 10:
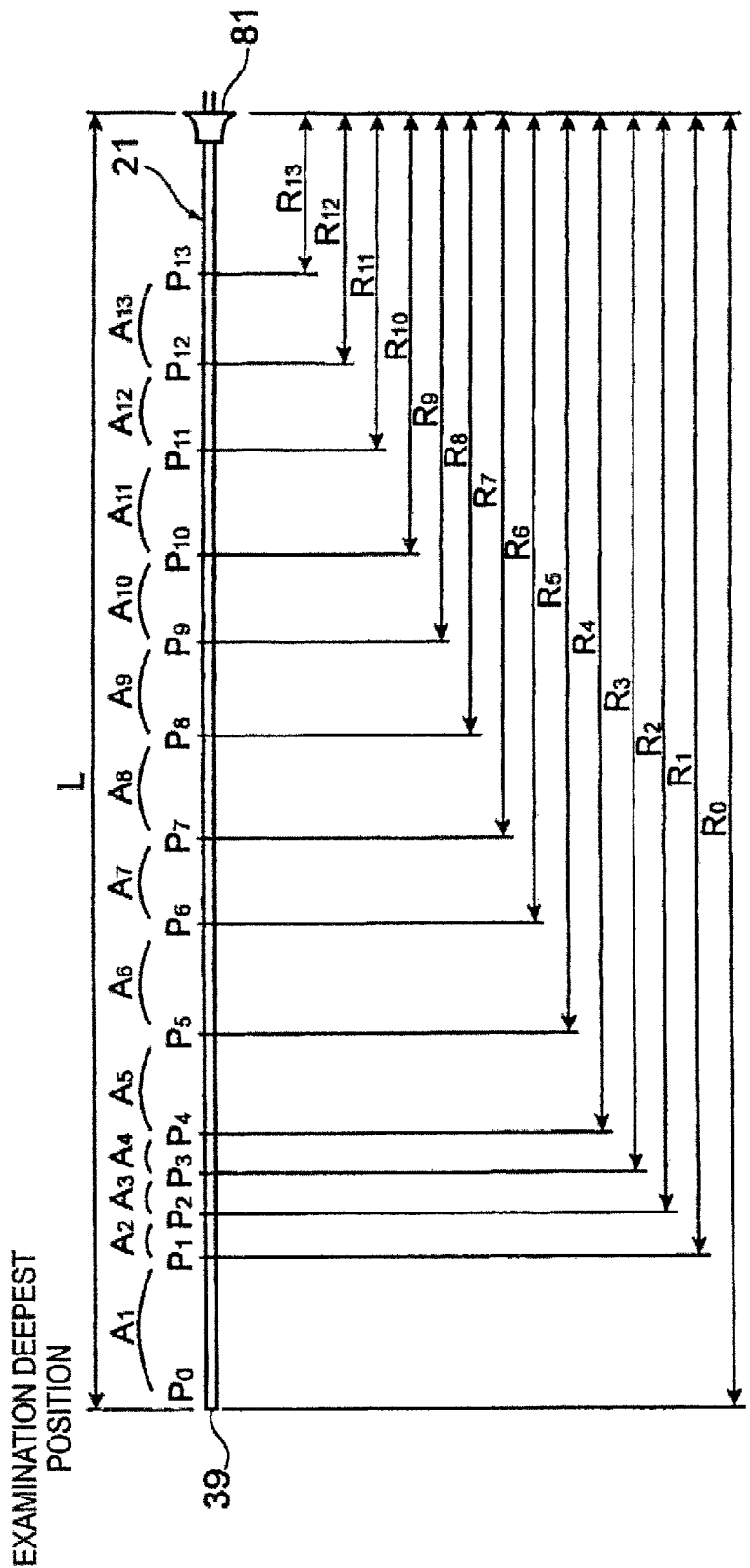
FIG. 10 schematically illustrates a relationship between insertion lengths of the endoscope insertion unit and positions of respective examination parts in a body cavity.

FIG. 10 schematically shows a relationship between insertion lengths of the endoscope insertion unit 21A and positions P0-P13 of respective examination parts in a body cavity. The positions P0-P13 of the examination parts in the body cavity can be represented by insertion lengths of the endoscope insertion unit 21A, respectively. In FIG. 10, the positions P0-P13 in the body cavity are shown in order, the position P0 being the position of the endoscope tip portion 39 inserted deepest. The insertion lengths of the endoscope insertion unit 21A in the body cavity are represented by their actual ratios R0-R13 to a maximum insertion length L that is equal to the distance between the position of the mouthpiece 81 and the detected examination deepest position P0. The examination deepest position P0 is the position of the examination part (the postbulbus of the duodenum and a lower part A1 (see Table 1)) for which an imaging instruction is to be given first after insertion of the endoscope insertion unit 21A into the body cavity.

In the embodiment, after the operator inserted the endoscope insertion unit 21A into the body cavity and advanced it to the examination deepest position P0, the endoscope tip position detecting means detects a maximum insertion length L and the control section 49 of the endoscope control apparatus 13 determines actual ratios R0-R13 of examination parts A1-A13. As a result, the endoscope tip portion 39 can be moved to the next examination position that is represented by an actual ratio.

Whether or not the endoscope tip portion 39 has reached the position of the actual ratio is judged by the endoscope control apparatus 13 based on a detection signal that is output from the mouthpiece 81. A still image of the examination part is taken based on an imaging control signal that is output from the endoscope control apparatus 13 when the endoscope tip portion 39 has reached the position of the actual ratio or a position having a prescribed degree of closeness to the position of the actual ratio.

More specifically, when receiving a detection signal indicating detection of a marking portion 85 from the mouthpiece 81 as the endoscope insertion unit 21A is moved by a manipulation of the operator, the endoscope control apparatus 13 converts the received detection signal into an insertion length of the endoscope insertion unit 21A and determines a detection ratio which is a ratio to the maximum insertion length L. When the detection ratio has become equal to a predetermined actual ratio of an examination part or a value corresponding to a predetermined degree of closeness, the endoscope control apparatus 13 outputs an imaging control signal.

The endoscope system 200 is provided with plural control modes for performing still image taking when an imaging control signal is output from the endoscope control apparatus 13.

In the first mode, when an imaging control signal is output from the endoscope control apparatus 13, a message to the effect that the endoscope tip portion 39 has reached an examination position is displayed on the display unit 15 to urge the operator to take a still image. This mode makes it possible to notify the operator reliably that the endoscope tip portion 39 has reached an examination part because a message to that effect is displayed on the display unit 15 the operator is watching steadily during the endoscopic examination.

In the second mode, when an imaging control signal is output from the endoscope control apparatus 13, the imaging unit is caused to take a still image and output the still image taken. Since the endoscope 11A takes a still image automatically without any imaging manipulation by the operator, the operator can concentrate on placing the observation subject in the imaging field of view.

In either mode, an alert is generated in the same manner as described above if the number of images taken is not equal to a preset number of images that should have been taken when the endoscope tip portion 39 is located at the current examination part. The notifying means for notifying the operator a fact that the number of images taken is in shortage may be any of the various means described above. The operator can switch between the above modes freely using the main body manipulation unit 19 of the endoscope 11A or the endoscope control apparatus 13.

Figure 11:
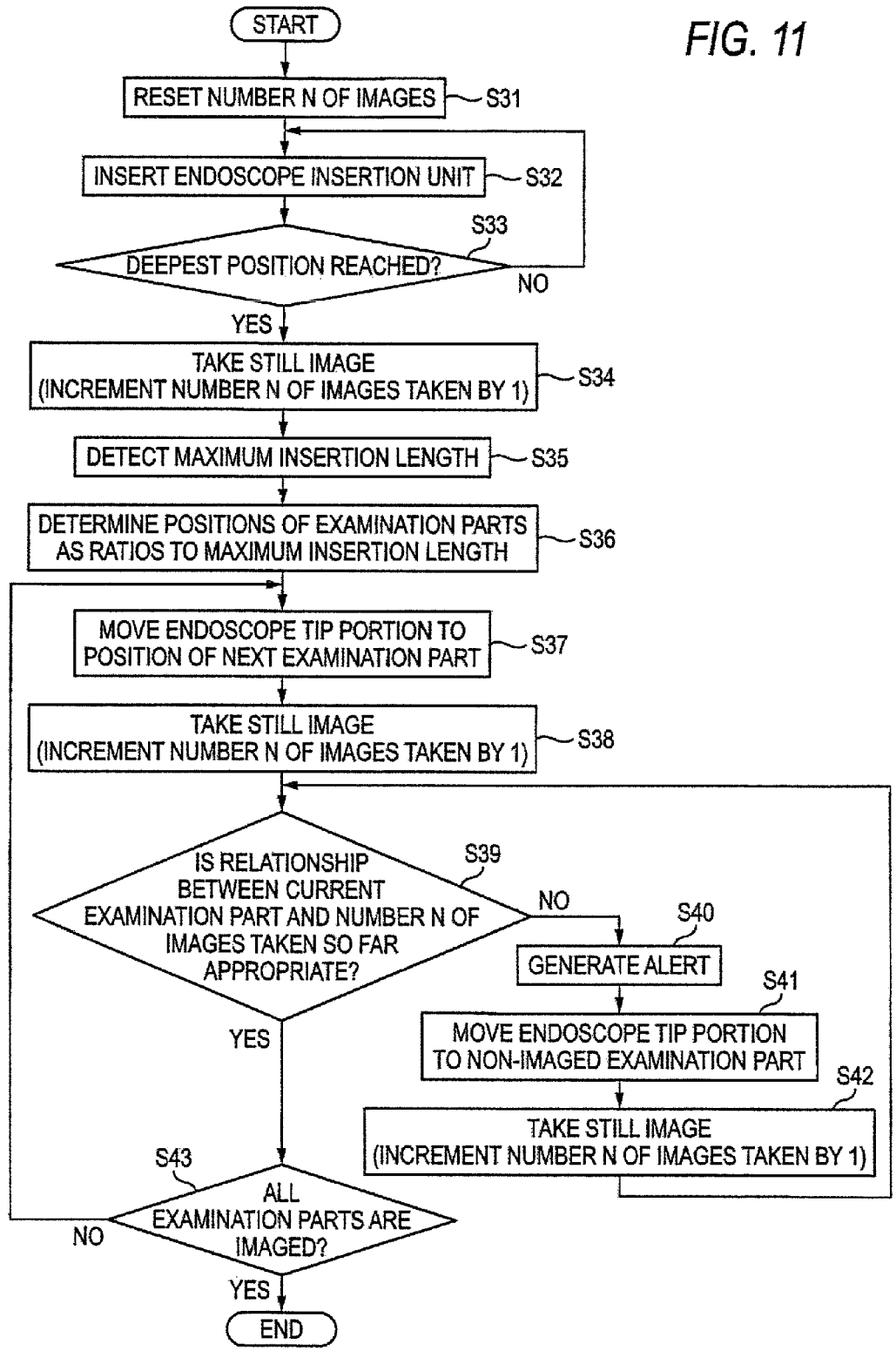
FIG. 11 is a flowchart of an endoscopic examination procedure of the endoscope system according to the second embodiment.

FIG. 11 is a flowchart of an endoscopic examination procedure of the endoscope system 200 according to the embodiment. A procedure for performing an endoscopic examination on the examination parts shown in Table 1 will be described with reference to FIG. 11.

As in the procedure of FIG. 6, first, after prescribed pre-examination treatment has been given to a patient, at step S31 the control section 49 resets the count of the number-of-images counter 51. At step S32, the operator of the endoscope 11A has the patient hold the mouthpiece 81 in his or her mouth and inserts the endoscope insertion unit 21A into the body cavity through the insertion hole 83 of the mouthpiece 81. The operator advances the endoscope insertion unit 21A until the endoscope tip portion 39 reaches the examination deepest position P0 (the postbulbus of the duodenum or lower) of the body cavity of the patient while checking observation images that are output from the endoscope 11A and displayed on the display unit 15 (step S33).

As the endoscope insertion unit 21A is inserted into the body cavity, detection signals of detection of marking portions 85 are output from the marking reading unit 87 of the mouthpiece 81 to the endoscope control apparatus 13. The endoscope control apparatus 13 converts the received detection signals into insertion lengths of the endoscope insertion unit 21A in the body cavity and thereby detects the insertion lengths in real time. That is, the endoscope control apparatus 13 detects sequential manipulations that are performed by the operator to insert the endoscope insertion unit 21A into the body cavity of the patient and thereby monitors insertion lengths of the endoscope insertion unit 21A in the body cavity.

After the endoscope tip portion 39 reached the examination deepest position P0, at step S34 the operator takes a still image by pushing the shutter button which is one of the manipulation buttons 27 of the main body manipulation unit 19 of the endoscope 11A. A resulting shutter button pushing signal is sent to the endoscope control apparatus 13 as a first imaging instruction signal. Triggered by the first imaging instruction signal, at step S35 the endoscope control apparatus 13 detects an insertion length of the endoscope insertion unit 21A that has been inserted to the examination deepest position P0. The thus-determined insertion length is stored in the endoscope control apparatus 13 as a maximum insertion length L.

At step S36, the endoscope control apparatus 13 converts the positions P1-P13 of the examination parts in the body cavity using the detected maximum insertion length L. The positions P1-P13 of the examination parts in the body cavity stored in the storage unit 53 are average positions of adult humans and herein called "standard positions in the body cavity." The standard positions in the body cavity do not necessarily coincide with actual positions of the patient body but are just rough measures. In view of this, the standard positions in the body cavity are converted into insertion lengths (standard insertion lengths) of the endoscope insertion unit 21A, which are then converted into actual ratios of the patient to the maximum insertion length L. The thus-determined actual ratios are correct pieces of position information that represent the positions of the examination parts in the body cavity in such a manner as to be suitable for the patient body.

After the determination of the actual ratios of the insertion lengths of the endoscope insertion unit 21A which represent the positions of the examination parts, at step S37 the operator moves the endoscope tip portion 39 to the next region A2 from the examination deepest position P0.

Figure 12:
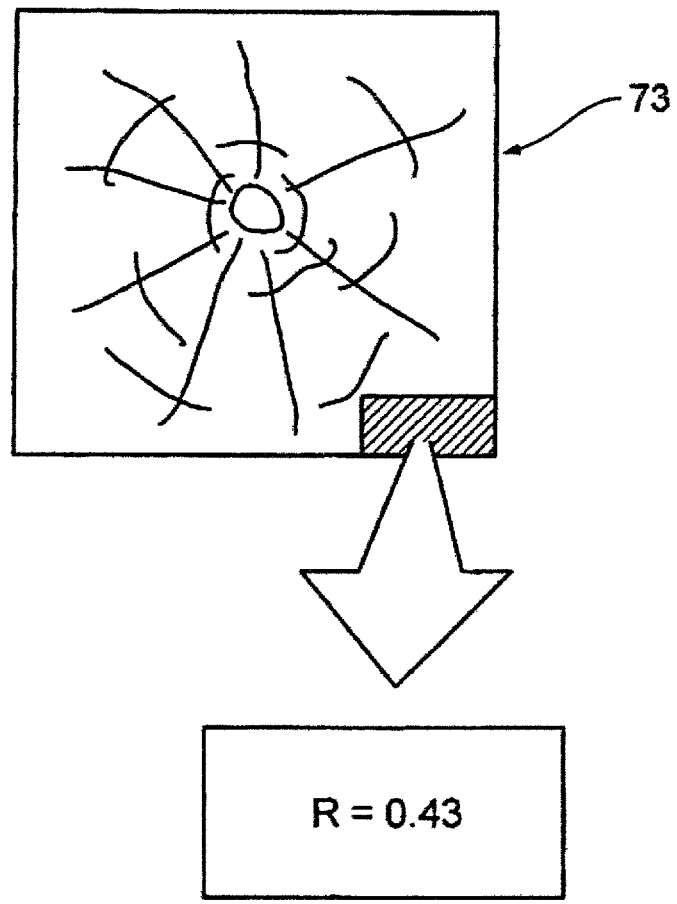
FIG. 12 shows an example picture displayed on the display unit.

At this time, as shown in FIG. 12, the endoscope control apparatus 13 displays, on the display unit 15, the detection ratio R representing the current observation position together with an observation image 73 so that the operator can recognize the position of the examination part more easily. Recognizing the detection ratio R together with the observation image 73, the operator can easily move the endoscope tip portion 39 so that the detection ratio R which varies with the insertion length of the endoscope insertion unit 21A in the body cavity comes closer to the actual ratio of the next examination part.

When the detection ratio R which varies every time the endoscope insertion unit 21A is moved becomes equal to the actual ratio of the next examination part or a value corresponding to a prescribed degree of closeness, at step S38 the operator stops moving the insertion of the endoscope insertion unit 21A and takes a still image of the examination part. The control section 49 increment the count of the number-of-images counter 51 by 1. When still image taking has been performed at region A2, the count of the number-of-images counter 51 is incremented to "2."

To proceed to still image taking of the third or following examination part, at step S39 whether the number of still images taken so far is appropriate or not is judged by referring to the actual ratios of the respective examination parts that are stored in the storage unit 53. For example, when a still image of region A3 has been taken, the count of the number-of-images counter 51 should be "3." If it is some other number such as "2" (S39: no), an alert is generated at step S40 with a judgment that a failure to image occurred. The alert is not described here because it may be generated in the same manners as described above.

If an alert is generated because of non-coincidence between the number of images taken and the preset number of images to be taken, at step S41 the operator determines an examination part for which he or she failed to take a still image by manipulating the endoscope control apparatus 13 and moves the endoscope tip portion 39 there. At step S42, the operator takes a still image. The operator can return to the desired examination part easily and reliably by moving the endoscope tip portion 39 while checking the relationship between the detection ratio and the actual ratio. After the still image taking, the control section 49 causes the number-of-images counter 51 to increment the number N of still images taken by 1.

Figure 13:
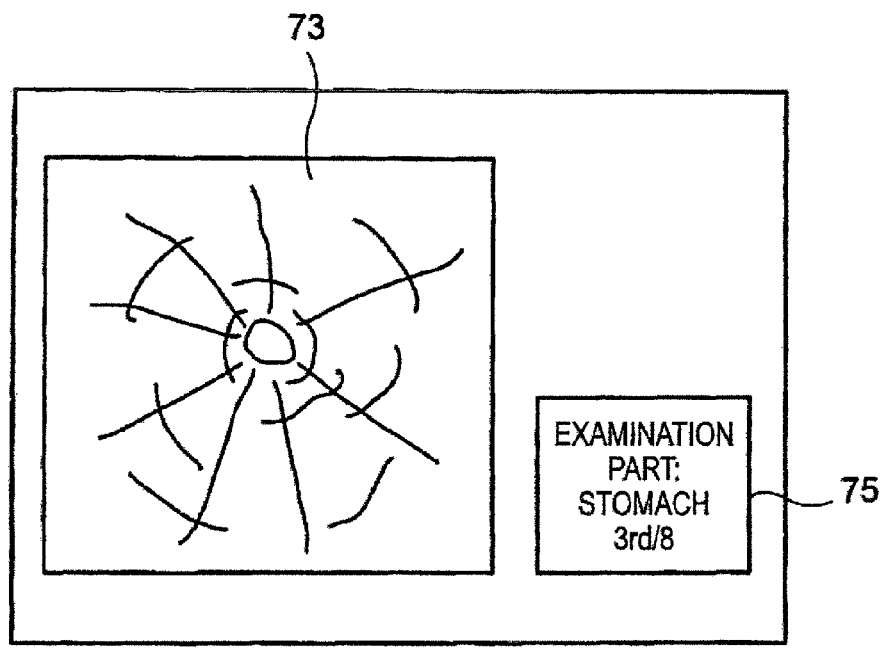
FIG. 13 shows another example picture displayed on the display unit.

Steps S37-S39 are executed repeatedly for all the examination parts excluding the first one. During that course, as shown in FIG. 13, an observation image 73 and interim information 75 are displayed on the display unit 15. The name of the organ (e.g., stomach) including the current examination part, the total number of still images to be taken for that organ (eight in the case of the stomach), and where the last image taken stands in the order of still images to be taken for that organ may be displayed together as the interim information 75. Alternatively, as shown in FIG. 7, the number of images taken so far and the number of all examination parts may be displayed.

Since the number of still images taken so far and a preset number of images to be taken are displayed together for each organ, the operator can easily recognize to what extent still image taking for each organ has proceeded.

The endoscope control apparatus 13 finishes the examination if it is judged that the relationship between the current examination part and the number of still images taken so far is appropriate (S39: yes) and still images have been taken for all the examination parts (S43: yes).

As described above, in the endoscope system 200, the current position of the endoscope tip portion 39 in a body cavity is recognized based on an insertion length of the endoscope insertion unit 21A by detecting it with the marking reading unit 87 of the mouthpiece 81. The operator performs hand manipulations while checking the number of still images taken on an examination-part-by-examination-part basis. Since the position of the endoscope tip portion 39 in a body cavity can be recognized, whether the number of images taken so far is appropriate can be checked with any timing during a series of hand manipulations. When a shortage has occurred in the number of images taken, the shortage can be detected early after its occurrence. As a result, the length by which the endoscope tip portion 39 should be moved to reach a re-imaging position can be reduced and the operator can perform hand manipulations with the endoscope 11A more smoothly.

Pieces of information of detection ratios representing insertion lengths of the endoscope insertion unit 21 and actual ratios representing positions of examination parts are recorded together with still images taken. The still images taken and various kinds of information are stored in the endoscope control apparatus 13, a server (not shown) connected to it, or a like apparatus and will be used in writing an endoscopic examination report of examination results. Since still images taken of a patient are recorded together with detection ratios and actual ratios corresponding to examination parts, in the next endoscopic examination imaging can easily be performed at the same positions as has been performed this time. Therefore, images to be taken next time will easily be compared with images taken this time, making it possible to diagnose variations of a diseased part more correctly.

In an endoscopic examination, the type of the endoscope in use can be identified by referring to actual ratios that represent positions of examination parts of a past endoscopic examination. That is, by checking the maximum insertion lengths L of endoscope insertion units 21, a usable endoscope can be determined from various endoscopes whose insertion units 21 have different total lengths. This facilitates apparatus management such as reservations for endoscopes.

As described above, the endoscope systems 100 and 200 according to the embodiments make it possible to acquire pieces of image information of desired examination parts reliably by imaging predetermined examination parts simply and reliably (i.e., without failing to image some of them) without the need for using a large-scale apparatus or making a lot of preparations. In the event of a shortage in the number of still images taken, an alert is generated during a series of hand manipulations of an endoscopic examination or immediately before the end of an examination to urge the operator to perform re-imaging. This allows the operator to avoid re-inserting the endoscope insertion unit 21 or 21A into the body cavity of a patient to perform re-imaging after removing it. The load on the patient can thus be reduced.

The above-described controls according to the image acquisition assisting procedures shown in the flowcharts of FIGS. 6 and 11 may be performed in the following manner. Programs for controlling the control section 49 are stored in the storage unit 53 (memory) in advance. One of the programs is selected by a proper manipulation on the endoscope 11 or 11A or the endoscope control apparatus 13, and the selected program is run by a CPU of the control section 49.

The invention is not limited to the above embodiments. A person skilled in the art would be able to modify or apply them based on the disclosure of the specification and known techniques, and such modifications and applications are also included in the range of protection. For example, although in the above embodiments a still image of each examination part is taken, a moving image may be taken instead. The installation position of the marking reading unit 87 is not limited to the mouthpiece 81; the marking reading unit 87 may disposed at any position as long as it enables measurement of positions of the endoscope tip portion 39 relative to a body cavity.

As described above, the following items are disclosed in the specification.

(1) An endoscope system sequentially images plural predetermined examination parts of a patient and thereby acquires still images of the respective examination parts by inserting an endoscope insertion unit having an imaging optical system in its tip portion into a body cavity of the patient. The endoscope system includes a number-of-images counting unit, a number-of-images counting unit and an alert generating unit. The number-of-images counting unit counts the number of still images taken every time one of the predetermined examination parts is imaged. The number-of-images comparing unit compares the counted number of still images with a preset number of images which corresponds to the number of the plural predetermined examination parts. The alert generating unit generates an alert when the number-of-images comparing unit detects non-coincidence between the counted number of still images taken and the preset number.

In this endoscope system, if the number of images taken that is counted by the number-of-images counting means is not equal to the preset number, an alert is generated to notify the operator of the non-coincidence. This makes it possible to acquire pieces of image information of desired examination parts correctly and rapidly by imaging predetermined examination parts simply and reliably (i.e., without failing to image some of them) without the need for using a large-scale apparatus or making a lot of preparations.

(2) The endoscope system according to (1) further includes an examination position information storage unit, an endoscope tip position detecting unit and a control unit. The examination position information storage unit stores positions of the predetermined examination parts in the body cavity. The endoscope tip position detecting unit detects a position, in the body cavity, of the tip portion of the endoscope insertion unit which is inserted in the body cavity. The control unit identifies a current examination part based on the position of the tip portion of the endoscope insertion unit detected by the endoscope tip position detecting unit by referring to the examination position information storage unit, and determines a preset number of images which should have been taken when imaging of the identified examination part is completed.

In this endoscope system, a position, in the body cavity, of the tip portion of the endoscope insertion unit is recognized and a counted number of images taken is compared with a preset number of images that should have been taken when a current examination part is imaged. An alert is generated if non-coincidence is found between the two numbers of images. As a result, when a shortage has occurred in the number of images taken, an alert can be generated early, whereby hand manipulations necessary for re-imaging can be reduced.

(3) The endoscope system according to (2), the endoscope tip position detecting unit detects a position, in the body cavity, of the tip portion of the endoscope insertion unit by detecting a relative positional relationship between the endoscope insertion unit and an insertion guide tool.

According to this endoscope system, since a position, in the body cavity, of the tip portion of the endoscope insertion unit is directly detected from a relative positional relationship between the endoscope insertion unit and the insertion guide tool, high position detection accuracy can be attained with a simple structure.

(4) The endoscope system according to (1), the number-of-images comparing unit compares the counted number of still images with the preset number after completion of imaging of a last one of the predetermined examination parts.

According to this endoscope system, imaging can be performed continuously (i.e., without stops) until a still image of the last examination part is taken. Therefore, as long as there occurs no failure to image, an endoscopic examination can be finished earliest.

(5) The endoscope system according to any one of (1) to (4) further includes a display unit. The display unit displays image information taken by the imaging optical system and the number of still images taken.

According to this endoscope system, since the number of images taken is displayed on the display unit, the operator can recognize a current observation position easily.

(6) The endoscope system according to (5), the display unit simultaneously displays the number of still images taken and a preset number of images which should have been taken when imaging of a current examination part is completed.

According to this endoscope system, the operator can recognize the degree of progress of an endoscopic examination more easily and hence is more apt to realize occurrence of a failure to image even halfway in the examination.

(7) The endoscope system according to (5), the display unit simultaneously displays the number of still images taken and a total number of still images which corresponds to the number of the plural predetermined examination parts.

According to this endoscope system, the operator can recognize the degree of progress of an endoscopic examination more easily and hence is more apt to realize occurrence of a failure to image even before imaging of the last examination part.

(8) The endoscope system according to any one of (5) to (7), the alert generating unit causes the display unit to display alert information indicating occurrence of the non-coincidence.

According to this endoscope system, since alert information is displayed on the display unit, it is possible to reliably notify the operator of inappropriateness of the number of images taken.

(9) The endoscope system according to any one of (1) to (7), the alert generating unit generates an alert by lighting a light-emitting device.

According to this endoscope system, since an alert is generated by lighting the light-emitting device, it is possible to notify the operator visually and hence to prevent a patient from feeling anxious unnecessarily.

(10) The endoscope system according to any one of (1) to (7), the alert generating unit generates an alert sound.

According to this endoscope system, since an alert sound is generated, it is possible to reliably notify not only the operator but also persons around the operator of a shortage in the number of images taken.

(11) An endoscope image acquisition assisting method sequentially images plural predetermined examination parts of a patient and thereby acquires still images of the respective examination parts by inserting an endoscope insertion unit having an imaging optical system in its tip portion into a body cavity of the patient. The endoscope image acquisition assisting method includes: counting the number of still images taken every time one of the predetermined examination parts is imaged; comparing the counted number of still images with a preset number of images which corresponds to the number of the plural predetermined examination parts; and generating an alert when non-coincidence is detected between the counted number of still images taken and the preset number.

In this endoscope image acquisition assisting method, if the number of images taken that is counted by the number-of-images counting means is not equal to the preset number, an alert is generated to notify the operator of the non-coincidence. This makes it possible to acquire pieces of image information of desired examination parts correctly and rapidly by imaging predetermined examination parts simply and reliably (i.e., without failing to image some of them) without the need for using a large-scale apparatus or making a lot of preparations.

(12) The endoscope image acquisition assisting method according to (11) further includes: storing, in an examination position information storage unit, positions of the predetermined examination parts in the body cavity; detecting a position, in the body cavity, of the tip portion of the endoscope insertion unit which is inserted in the body cavity; and identifying a current examination part based on the detected position of the tip portion of the endoscope insertion unit by referring to the examination position information storage unit; and determining a preset number of images which should have been taken when imaging of the identified examination part is completed.

In this endoscope image acquisition assisting method, a position, in the body cavity, of the tip portion of the endoscope insertion unit is recognized and a counted number of images taken is compared with a preset number of images that should have been taken when a current examination part is imaged. An alert is generated if non-coincidence is found between the two numbers of images. As a result, when a shortage has occurred in the number of images taken, an alert can be generated early, whereby hand manipulations necessary for re-imaging can be reduced.

(13) The endoscope image acquisition assisting method according to (11), the comparing step compares the counted number of still images taken with the preset number after completion of imaging of all of the predetermined examination parts. The generating step generates an alert when non-coincidence is detected between the counted number of still images taken and the preset number.

In this endoscope image acquisition assisting method, imaging can be performed continuously (i.e., without stops) until a still image of the last examination part is taken. Therefore, as long as there occurs no failure to image, an endoscopic examination can be finished earliest.

(14) A non-transitory computer readable medium causes a computer to execute a process of the endoscope image acquisition assisting method according to any one of (11) to (13).

In this program, the number of still images taken is checked in an endoscopic examination in which observation subjects are determined in advance. An alert is generated if the number of still images taken is in shortage. This enables the operator to perform re-imaging.

Figure 14:
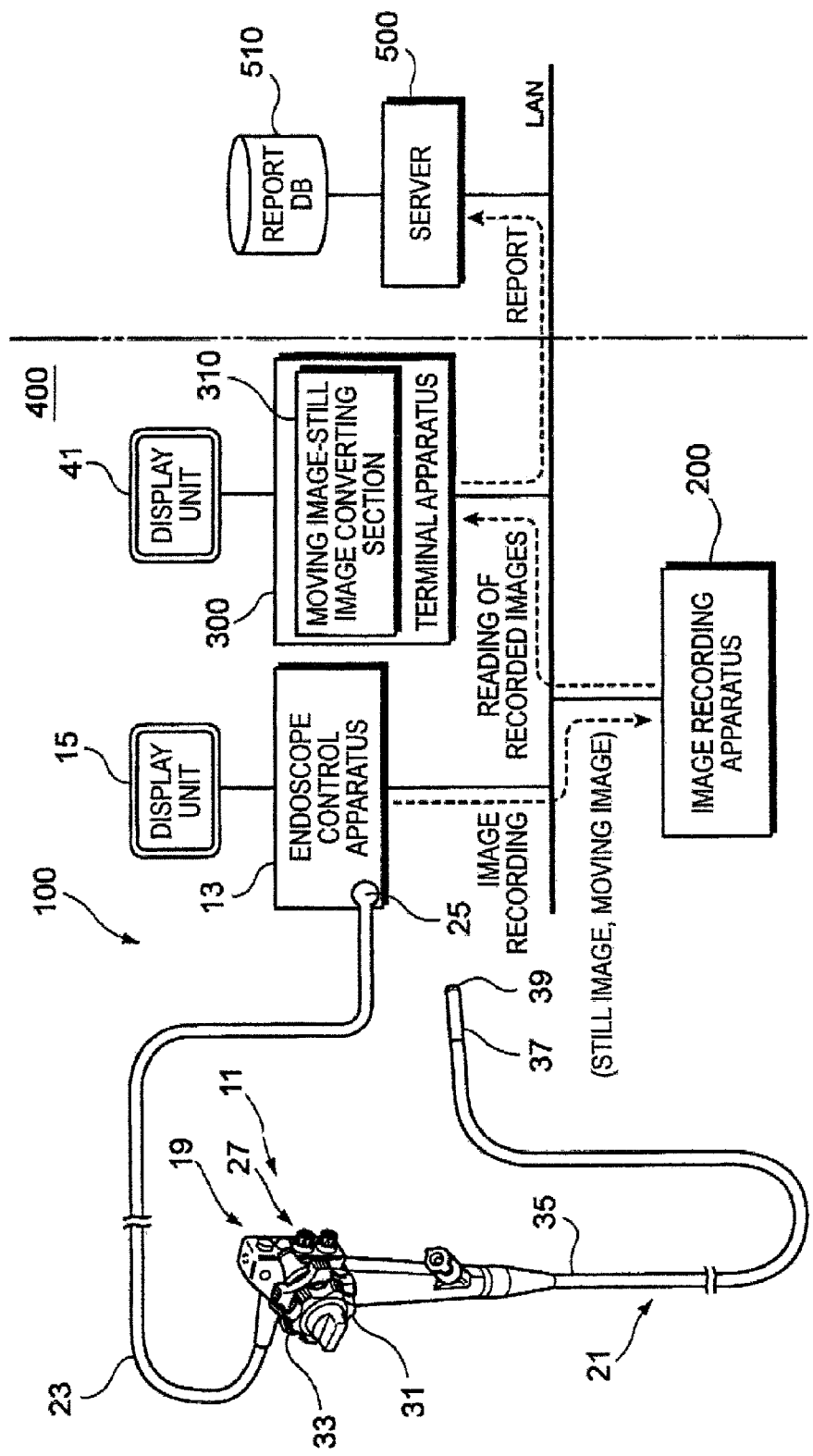
FIG. 14 shows the configurations of an endoscope image recording apparatus including an endoscope system and the entire intra-hospital system according to a third embodiment.

A third embodiment of the present invention will be hereinafter described in detail with reference to the drawings. FIG. 14 shows the configurations of an endoscope image recording apparatus including an endoscope system and the entire intra-hospital system according to the third embodiment.

The intra-hospital system is configured as follows. The endoscope image recording apparatus 400 which is equipped with the endoscope system 100, an image recording apparatus 200, and a terminal apparatus 300 is installed in an endoscope section. A server 500 is connected to the individual apparatus of the endoscope image recording apparatus 400. Connected to each other by a network, the individual apparatus of the endoscope image recording apparatus 400 can communicate with each other. A report database 510 is connected to the server 500.

The endoscope system 100 is equipped with an endoscope 11 having an imaging optical system and an illumination optical system, an endoscope control apparatus 13 as a control means for controlling the endoscope 11, and a display unit 15 for displaying image information etc. The endoscope control apparatus 13 which is connected to the endoscope 11 is connected to the image recording apparatus 200, the terminal apparatus 300 and a server 500 via a network and hence can receive and output various kinds of information.

The endoscope 11 is equipped with a main body manipulation unit 19 and an endoscope insertion unit 21 which is continuous with the main body manipulation unit 19 and is to be inserted into a body cavity. One end of a universal cord 23 is connected to the main body manipulation unit 19, and the other end of it is connected to the endoscope control apparatus 13 by a connector 25.

Various manipulation buttons 27 such as buttons for performing suction, air feed, and water feed at the tip (located on the side that is more distant from the main body manipulation unit 19) of the endoscope insertion unit 21, a shutter button for imaging and procedure exit button for notifying an ending of the procedure are arranged on the main body manipulation unit 19 of the endoscope 11, and a pair of angle knobs 31 and 33 are attached to the main body manipulation unit 19.

The endoscope insertion unit 21 is composed of a soft portion 35, a curved portion 37, and a tip portion (hereinafter referred to as an endoscope tip portion) 39. A curving manipulation can be performed on the curved portion 37 remotely by rotating the angle knobs 31 and 33 of the main body manipulation unit 19, whereby the endoscope tip portion 39 can be directed to a desired direction.

The endoscope tip portion 39 (not shown) is provided with an observation window of the imaging optical system and light emission windows of the illumination optical system. The imaging optical system is configured to image reflection light from an observation subject region (in a body cavity) being illuminated with illumination light beams that are emitted from the light emission windows.

Being an imaging unit having an imaging device such as a CCD (charge-coupled device) or a CMOS (complementary meta-oxide-semiconductor) sensor and optical members such as an image-forming lens disposed in front of the imaging device on its optical path, the imaging optical system acquires an observation image through the observation window and outputs a resulting imaging signal. The imaging signal is transmitted to the endoscope control apparatus 13 by the universal cord 23, subjected to proper image processing that is performed by an image processing circuit of the endoscope control apparatus 13. A resulting image is displayed on the display unit 15.

The illumination optical system of the endoscope 11 guides, to the endoscope tip portion 39, illumination light that is transmitted from the endoscope control apparatus 13 via the universal cord 23, and emits resulting light beams to an observation subject region through the light emission windows. A white light source such as a xenon lamp, a halogen lamp, or a metal halide lamp, a laser light source, a semiconductor light-emitting device such as a light-emitting diode, or a like light source is provided in the endoscope control apparatus 13.

To perform an endoscopic examination using the above-configured endoscope system 100, the operator of an endoscope inserts the endoscope insertion unit 21 into the body cavity of a patient (subject person) and images predetermined examination parts sequentially while adjusting the position of the endoscope tip portion 39 which incorporates the imaging unit. Image data obtained by this examination (imaging) are supplied from the endoscope system 100 to the image recording apparatus 200 and stored there. The stored image data will be used later in writing a report of endoscopic examination results.

The image data that are recorded in the image recording apparatus 200 consist of moving image data and still image data. The image data is taken continuously at a constant frame rate (e.g., 30 frames/sec) from the start of an examination (i.e., the start of insertion of the endoscope insertion unit 21 into a body cavity (or arrival of the endoscope tip portion 39 to a first examination part)) to the end of the examination and recorded. The image data is data of a large number of image frames that are arranged in time series. Each of the still image data is taken with particular timing, for example, when a doctor manipulates a prescribed button (shutter button of the endoscope 11.

Among the image data recorded in the image recording apparatus 200, the still image data are dealt with as examination image data (i.e., image data of endoscopic examination results). In the endoscope image recording apparatus 400 according to the embodiment, if the number of still images recorded is smaller than a preset number, it is judged that a failure(s) to image occurred and assistance is made for addition of data of missing images to examination image data.

More specifically, the endoscope image recording apparatus 400 assists processing of extracting missing still images from already recorded moving image data. Where missing still images are generated based on already recorded moving image data, a complete set of necessary still images is always obtained and hence the accuracy of an endoscopic diagnosis is not lowered. Furthermore, the load on a patient can be reduced (e.g., an endoscopic re-examination for imaging missing images can be avoided).

The assistance will be outlined below. First, an examination order in which particulars of an endoscopic examination is transmitted from the server 500 to the terminal apparatus 300. An endoscopic examination is performed on a patient in the endoscope section based on the examination order. The examination order includes ID information of the patient and the patient is thereby identified.

The operator of the endoscope 11 performs an endoscopic examination on the designated patient according to the examination order. Resulting image data (still images and a moving image) that are output from the endoscope 11 is recorded in the image recording apparatus 200 together with the ID information of the patient. The image data can also be recorded in the endoscope control apparatus 13.

After completion of the endoscopic examination, the operator of the terminal apparatus 300 in the endoscope section reads out the image data of the patient recorded in the image recording apparatus 200, using the ID information as a tag and counts the number of recorded still image data that are included in the image data. The terminal apparatus 300 compares the number of recorded still images with the preset number specified in the examination order. If it is judged that the number of recorded still images in shortage, the terminal apparatus 300 displays, on a display unit 41, a message to the effect that number of recorded still images in shortage.

Looking at the above message, the operator of the terminal apparatus 300 reads out the moving image data of the image data recorded in the image recording apparatus 200 and extracts still images of scenes corresponding to the missing still images. A moving image-still image converting section 310 converts parts of the moving image into still images. Data of the thus-generated still images are incorporated into the existing still image data, whereby examination image data having the preset number of still image data is generated.

The examination image data is used for generating a report of endoscopic examination results in which pieces of position information indicating positions of imaging subjects are correlated with the respective examination images. Data of the report is transmitted from the terminal apparatus 300 to the server 500 and stored in the report database 510 as endoscopic examination results.

Next, a description will be made of a specific example of an examination procedure by which the above-configured endoscope image recording apparatus 400 performs an endoscopic examination on a patient.

FIGS. 4A-4C illustrate a procedure of an endoscopic examination of the upper digestive tract. In this example endoscopic examination of the upper digestive tract, first, as shown in FIG. 4A, the endoscope insertion unit 21 is inserted through the esophagus Es and the stomach St to an examination deepest position P0 in the duodenum Duo. When the endoscope insertion unit 21 has reached the examination deepest position P0, the operator takes a still image (observation image) there. Then, the operator moves the endoscope insertion unit 21 through the body cavity while pulling it gradually. In doing so, the operator shoots the region of the stomach St (see FIG. 4B) and the region of the esophagus Es (see FIG. 4C) in order. Finally, the operator withdraws the endoscope insertion unit 21 from the body cavity.

FIG. 5 and Table 2 show specific examination parts of the endoscopic examination to be performed by the above procedure. The endoscopic examination parts are divisional regions A1-A13, arranged in this order from the examination deepest position P0, of the duodenum Duo, stomach St, and esophagus Es.

TABLE 2

| Region | Name of examination part | Position in body cavity |
|---|---|---|
| A1 | Postbulbus of duodenum and lower part | P0-P1 |
| A2 | Duodenal bulb | P1-P2 |
| A3 | Pylorus front part | P2-P3 |
| A4 | Pylorus anterior wall | P3-P4 |
| A5 | Angular incisure | P4-P5 |
| A6 | Lower part of stomach body | P5-P6 |
| A7 | Middle part of stomach body | P6-P7 |
| A8 | Upper part of stomach body | P7-P8 |
| A9 | Fundus ventriculi (posterior wall of gastic fundus) | P8-P9 |
| A10 | Cardiac region of stomach | P9-P10 |
| A11 | Lower part of esophagus | P10-P11 |
| A12 | Middle part of esophagus | P11-P12 |
| A13 | Upper part of esophagus | P12-P13 |

The operator of the endoscope 11 moves the endoscope tip portion 39 to the individual examination parts and takes still images necessary for a diagnosis at the respective positions by pushing the shutter button. The endoscope control apparatus 13 records the still images of the respective examination parts in the image recording apparatus 200 together with the ID information for identification of the patient. Furthermore, video that is produced by the endoscope 11 from the start to the end of the endoscopic examination is output from the endoscope control apparatus 13 as data of a continuous image, that is, a moving image that varies with time, and recorded in the image recording apparatus 200 together with the ID information. That is, during the endoscopic examination, the moving image recorded parallel with the recording of the still images. The operator writes a report of the endoscopic examination using the terminal apparatus 300 based on the information (usually, only the still image data) recorded in the image recording apparatus 200.

Figure 15:
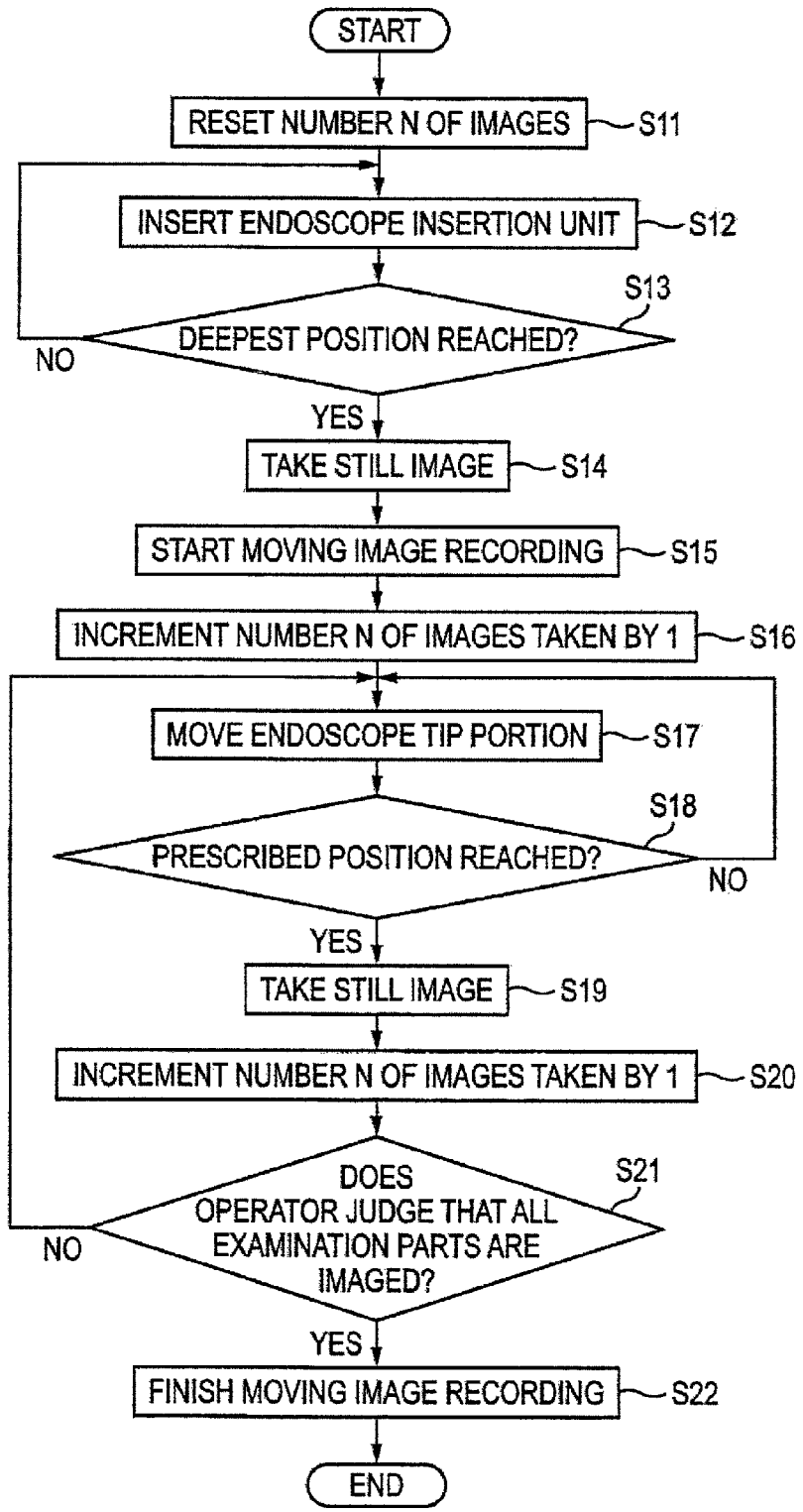
FIG. 15 is a flowchart of a procedure of an endoscopic examination of the upper digestive tract.

FIG. 15 is a flowchart of an endoscopic examination procedure. A procedure for performing an endoscopic examination on examination parts shown in Table 1 will be described with reference to FIG. 15. The procedure of FIG. 15 assumes that the endoscope control apparatus 13 has the function of a number-of-images counter for counting the number of still images taken and a current number of images taken can thereby be displayed on the display unit 15.

To perform an endoscopic examination, first, prescribed pre-examination treatment is given to a patient. Then, at step S11, the endoscope control apparatus 13 resets the count of the built-in number-of-images counter. At step S12, the operator of the endoscope 11 inserts the endoscope insertion unit 21 into the body cavity. The operator advances the endoscope insertion unit 21 until the endoscope tip portion 39 reaches an examination deepest position P0 (the postbulbus of the duodenum or lower; see FIG. 4A) of the body cavity of the patient while checking observation images that are output from the endoscope 11 and displayed on the display unit 15 (step S13).

After the endoscope tip portion 39 reached the examination deepest position P0, at step S14 the operator pushes the shutter button which is one of the manipulation buttons 27 of the main body manipulation unit 19 of the endoscope 11. A resulting shutter button pushing signal is sent to the endoscope control apparatus 13 as a first imaging instruction signal. At step S15, the image recording apparatus 200 starts recording a moving image.

The endoscope control apparatus 13 records, in the image recording apparatus 200, a still image of the examination part in region A1. Since this is the first still image taking, at step S16 the number-of-images counter of the endoscope control apparatus 13 automatically changes its count to "1." The count of the number-of-images counter is output to and displayed on the display unit 15.

After the end of the still image taking at region A1, at steps S17 and S18 the operator moves the endoscope tip portion 39 to the next region A2. At step S19, the operator takes a still image of the examination part in region A2 by pushing the shutter button. At step S20, the count of the number-of-images counter is incremented to "2."

Steps S17-S20 are executed for all the examination parts excluding the first one. During that course, the endoscope control apparatus 13 displays, on the display unit 15, an image being produced at the current position of the endoscope tip portion 39 and interim information including the number of images taken so far (i.e., the count of the number-of-images counter) and the total number of examination parts.

If judging that still image taking has been performed for all the examination parts (S21: yes), the operator pushes a hand manipulation end button which is one of the manipulation buttons 27. A resulting signal is input to the image recording apparatus 200 via the endoscope control apparatus 13, whereupon the image recording apparatus 200 finishes the moving image recording operation (step S22).

With the above procedure, the image recording apparatus 200 records a moving image continuously (started at step S15 and finished at step S22). That is, moving image data recorded in the image recording apparatus 200 includes all information of video that has been observed by the endoscope 11 from recording of a first still image to recording of a last still image. Each still image may be recorded together with information (metadata) indicating where the still image stands in the order of all still images. Information indicating the total number of still images taken may be recorded as part of the still image data.

The above examination example is just an example; in actual endoscopic examinations, as many as 20 to 30 still images may be taken in total. The numbers of still images to be taken are set in advance for respective organs or examination parts. If the number of still images taken is smaller than a preset number, a doctor cannot make a correct diagnosis because of an insufficient amount of information. That is, a doctor cannot make a correct diagnosis in a state that the number of still images recorded during an endoscopic examination is smaller than a preset number, that is, a failure(s) to image a still image occurred and is not compensated for yet. However, receiving an endoscopic examination again is a heavy load to the patient.

In view of the above, the endoscope image recording apparatus 400 according to the embodiment is provided with the assist function of adding missing still images without the need for performing an endoscopic examination again even in a situation that a failure(s) to image a still image occurred.

AS shown in FIG. 14, the endoscope image recording apparatus 400 is realized as functions of the endoscope system 100, the image recording apparatus 200, and the terminal apparatus 300. As described above, the image recording apparatus 200 is provided with a function of a data storage means for storing moving image data representing a moving image that is recorded continuously and still image data representing still images each of which is taken upon reception of a prescribed instruction (e.g., pushing of the shutter button).

The terminal apparatus 300 is provided with a function of a number-of-recorded-images detecting means for detecting the number of recorded still images, a function of a numberof-images comparing and judging means for comparing the number of recorded still images detected by the number-of-recorded-images detecting means with a total number of images to be taken that is set in advance according to examination conditions such as observation parts (imaging subjects), and judging whether or not the former is smaller than the latter, and a function of a signal output means for outputting an image acquisition assist signal for acquisition of missing still images if the number of recorded still images is judged smaller than the total number of images to be taken.

Figure 16:
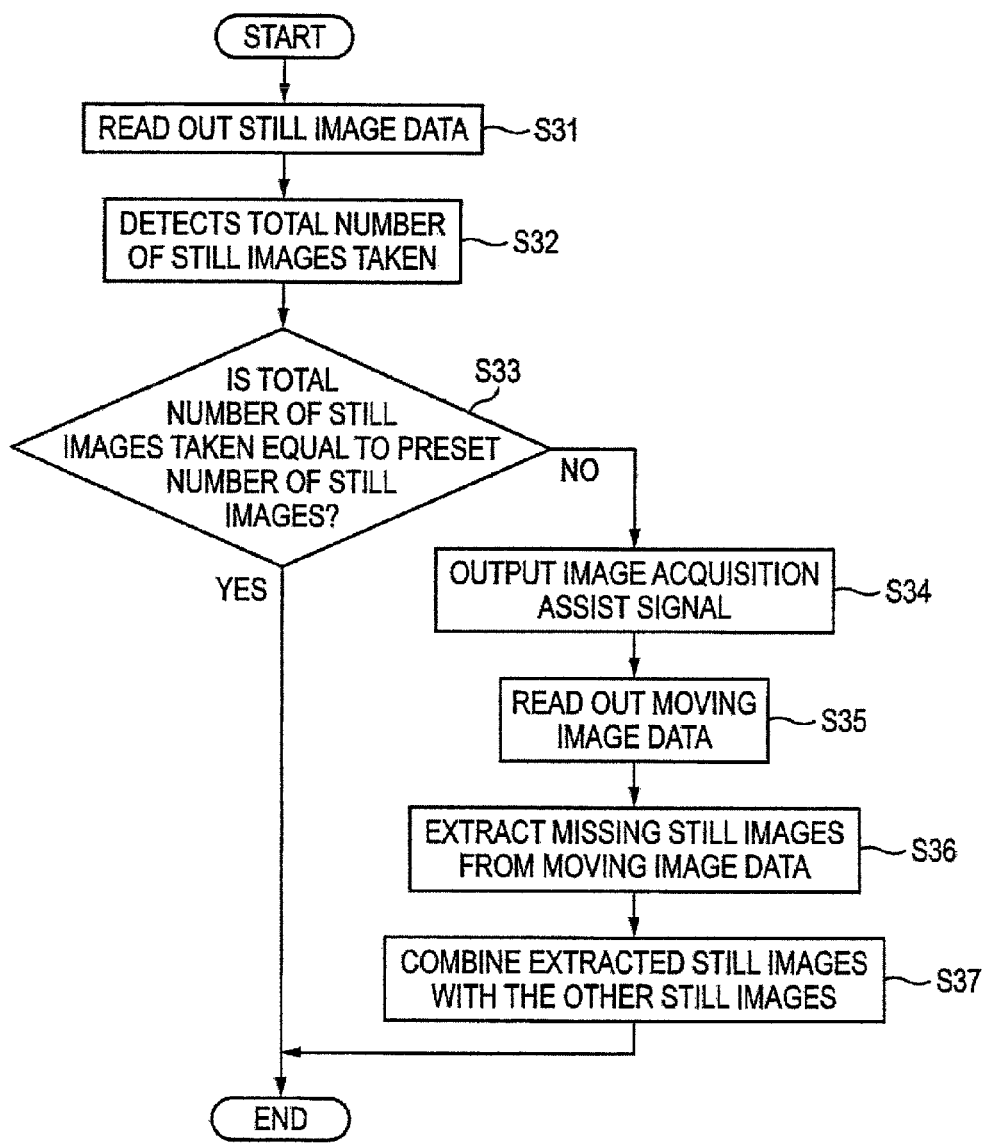
FIG. 16 is a flowchart of a main process which is executed by a terminal apparatus.

FIG. 16 is a flowchart outlining a process which is executed by the terminal apparatus 300. The process of FIG. 16 is executed after an endoscopic examination was performed on a patient and image data of still images and a moving image were recorded in the image recording apparatus 200.

First, at step S31, the terminal apparatus 300 accesses the image recording apparatus 200 via the network, retrieves image data which are results of an endoscopic examination performed on a particular patient based on ID information, and reads the still image data included in the retrieved image data from the image recording apparatus 200.

At step S32, the terminal apparatus 300 detects the number of still image data that were read out at step S31, as the total number of existing still images. For example, the total number of still images taken is determined by counting the number of still image files. Alternatively, where information indicating the total number of still images taken is recorded as part of the still image data, that information may be read out.

At step S33, the terminal apparatus 300 compares the total number of still images taken that was detected at step S32 with the total number of still images to be taken (the preset number of still images necessary for a diagnosis) that corresponds to the preset number of examination parts. The preset number of still images is set in advance according to an examination order of the patient concerned. For example, a patient is to receive an endoscopic examination of the upper digestive tract shown in Table 1, the 13 examination parts are set in advance, that is, the preset number of still images is 13. If the total number of still images taken is equal to the preset number of still images (S33: yes), the process is finished immediately because there is no shortage in the total number of still images taken.

If the total number of still images taken is smaller than the preset number of still images (S33: no), at step S34 the terminal apparatus 300 judges that a failure(s) to image a still image occurred and outputs an image acquisition assist signal for acquisition of missing still images.

At step S35, the terminal apparatus 300 accesses the image recording apparatus 200 via the network (LAN) and acquires all the moving image data that was recorded during the endoscopic examination of the patient concerned (i.e., the moving image that was taken from the start to the end of the examination).

At step S36, the moving image-still image converting section 310 of the terminal apparatus 300 extracts data corresponding to the missing still images from the moving image data that was acquired at step S34, and generates new still images.

Since the moving image data as the processing subject includes data of video that was taken from the start to the end of the examination, the moving image data includes pieces of information of particular image frames corresponding to the missing still images. Therefore, if examination parts of the missing still images are known, the corresponding image frames can be identified and pieces of information of still images can be extracted from the moving image data.

Since examination parts of the missing still images can be identified by various methods (described later), the moving image-still image converting section 310 (see FIG. 14) can automatically extracts missing still images from the moving image data. Naturally, for example, it is possible to generate still images from the moving image data by displaying information that is useful for extraction of still image data and determine image frames to be extracted according to manipulations of the operator who manipulates the terminal apparatus 300.

The same ID information as the ID information of the patient that is contained in the moving image data as the processing subject is assigned to the still images that were extracted at step S36 by the moving image-still image converting section 310. When a patient receives an endoscopic examination, ID information for identification of the patient is output from the server 500 and moving image data is recorded in the image recording apparatus 200 together with the ID information. Assigning the same ID information of the patient as the ID information contained the moving image data to still images extracted from the moving image data makes it possible to prevent an erroneous diagnosis.

At step S37, the terminal apparatus 300 combines the still images extracted at step S36 with the other still images that were read from the image recording apparatus 200 at step S31, and thereby establishes a state that resulting examination image data of the patient can be output. This examination image data is used in writing a report. In the report, pieces of position information of the examination images are recorded together with the examination images.

Figure 17:
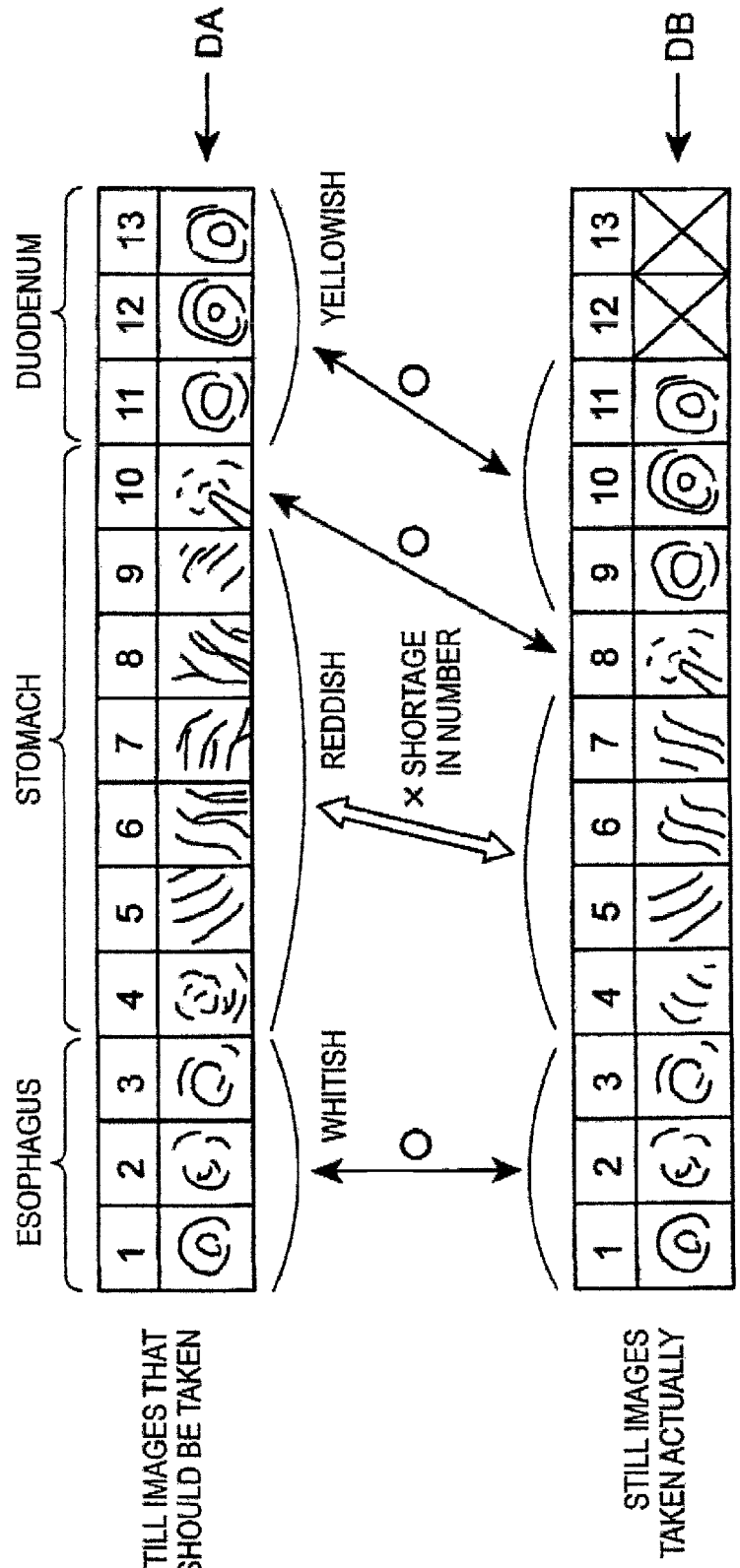
FIG. 17 schematically shows specific examples of still images that are recorded in the image recording apparatus during an endoscopic examination.

FIG. 17 schematically shows still images that are recorded in the image recording apparatus 200 during an endoscopic examination. This example assumes an endoscopic examination of the above-described upper digestive tract in which the 13 examination parts are set. It is necessary to record still images for the first to 13th examination parts, respectively, like a data group DA shown in the top part of FIG. 17. It is also assumed here that only 11 still images were recorded actually as a data group DB as shown in the bottom part of FIG. 17 because failures to image occurred in imaging the stomach.

When the terminal apparatus 300 processes the data of the still images, the fact that the total number (11) of still images taken is not equal to the preset number (13) of still images is detected at step S33 (see FIG. 16) and an image acquisition assist signal for addition of two missing still images is output.

The position of a missing still image can be determined easily if to what organ an imaging subject corresponding a missing still image belongs is determined. An organ to which the corresponding imaging subject belongs to can be determined automatically as described below.

<First Position Determining Method>

For example, in the case of an endoscopic examination of the upper digestive tract, images produced by imaging the esophagus (whitish), the stomach (reddish), and the duodenum (yellowish because of bile) are different from each other in hue.

Therefore, what organ was imaged to produce each still image is judged automatically or what part of an organ was imaged to produce each still image is judged roughly but automatically by collating pieces of hue information obtained by image-processing individual still images with the above-described features of the respective organs.

Such discrimination processing should lead to conclusions that the first to third still images of the data group DB shown in the bottom part of FIG. 17 correspond to the esophagus, the fourth to eighth still images correspond to the stomach, and the ninth to 11th still images correspond to the duodenum. Therefore, it is automatically found that two of seven still images that should be taken for the imaging parts of the stomach are missing. That is, in this example, a search range of moving image data from which to extract missing still images can be restricted to data of an imaging range of the stomach. In this manner, to what organ(s) missing still images correspond can be determined by determining the numbers of still images that are required for the respective organs, determining the numbers of still images that were taken actually for the respective organs, and comparing the two kinds of numbers for each organ.

To assist addition of missing still images, in this example, information to the effect that an imaging range corresponding to the missing still images is the stomach is given to the operator of the terminal apparatus 300 through a display or the like. The operator restricts the search range of moving image data to a range corresponding to the stomach.

<Second Position Determining Method>

Figure 18:
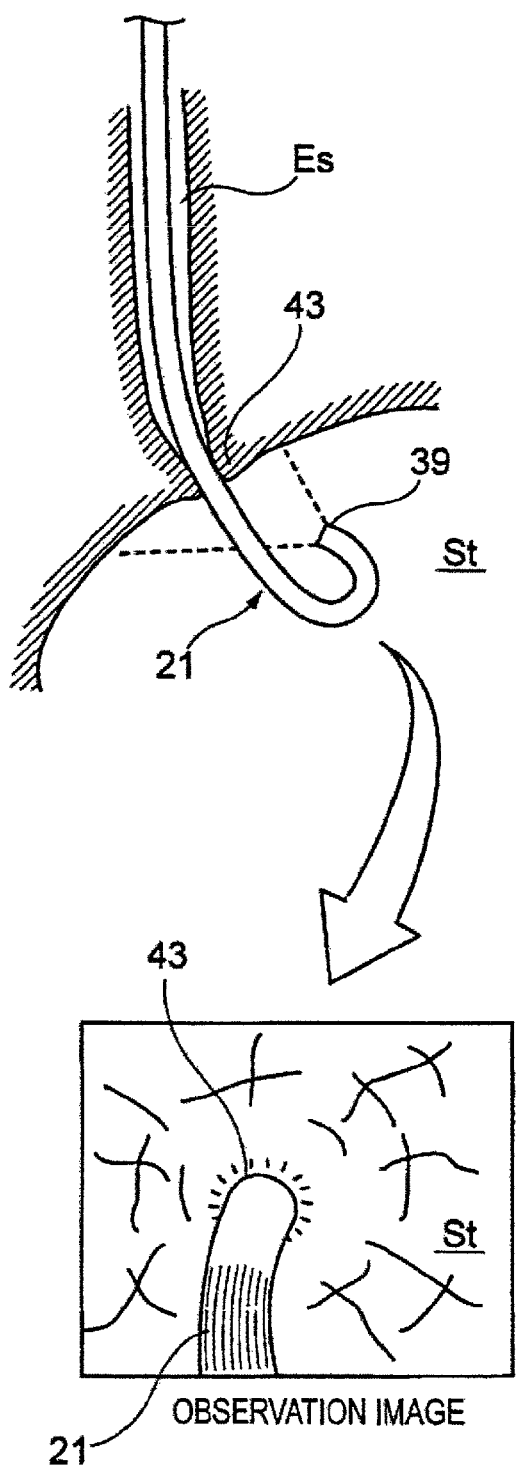
FIG. 18 schematically shows a shape of an endoscope insertion unit and its positional relationship with the cardiac region of stomach in imaging the cardiac region of stomach in a state that an endoscope tip portion is inserted in the stomach and an observation image that is produced in this state.

FIG. 18 schematically shows a shape of the endoscope insertion unit 21 and its positional relationship with the cardiac region of stomach 43 in imaging the cardiac region of stomach 43 in a state that the endoscope tip portion 39 is inserted in the stomach St and an observation image that is produced in this state.

The cardiac region of stomach 43 is imaged in such a manner that the endoscope tip portion 39 is curved to a large extent and a portion, behind the tip portion 39, of the endoscope insertion unit 21 is included in the field of view. Therefore, a portion of the endoscope insertion unit 21 appears in an image taken.

Whether or not a portion of the endoscope insertion unit 21 is included in an image taken can be detected by judging whether or not features (shape, color, etc.) of the endoscope insertion unit 21 are included in image pattern features that are extracted by image processing when the terminal apparatus 300 processes each still image or each frame of a moving image. In this manner, whether or not the examination part of an image concerned is the cardiac region of stomach 43 can be determined automatically. This processing can also be used for assisting addition of missing still images.

<Third Position Determining Method>

Position information that is correlated with an insertion length of the endoscope insertion unit 21 in a body cavity can be used for determining an imaging subject part when the endoscope insertion unit 21 is inserted into the body cavity. For example, an insertion length of an endoscope insertion unit 21A in a body cavity can be detected by using an endoscope 11A shown in FIG. 19 and a mouthpiece 51 shown in FIG. 20.

Figure 20:
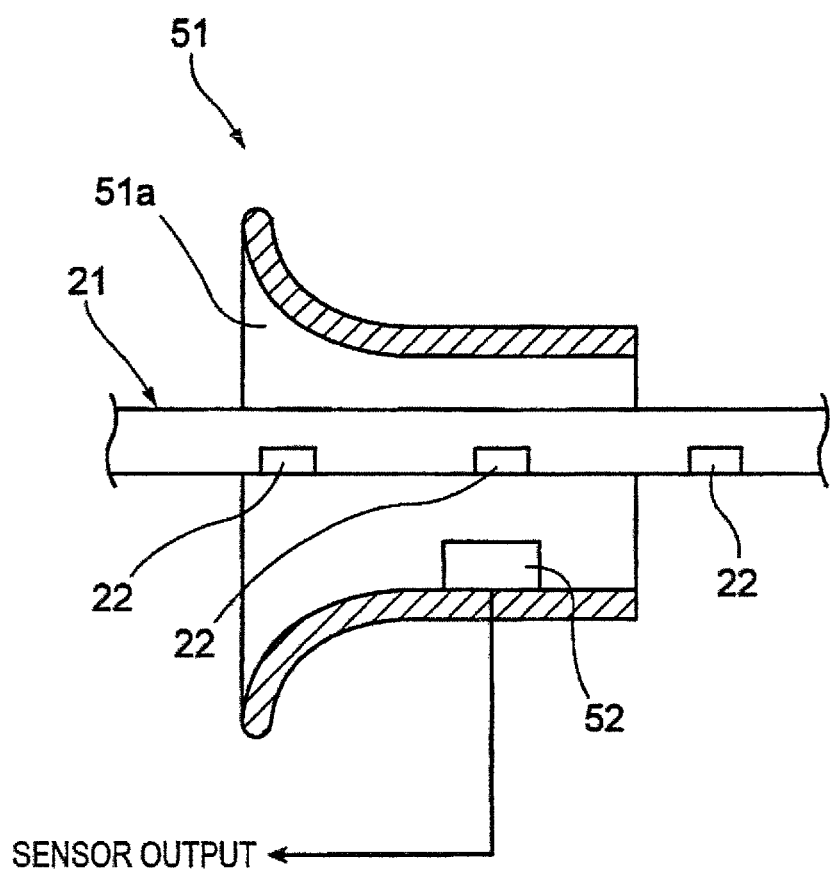
FIG. 20 is a sectional view of a mouthpiece to be used for detecting an insertion position of the endoscope insertion unit.
Figure 21:
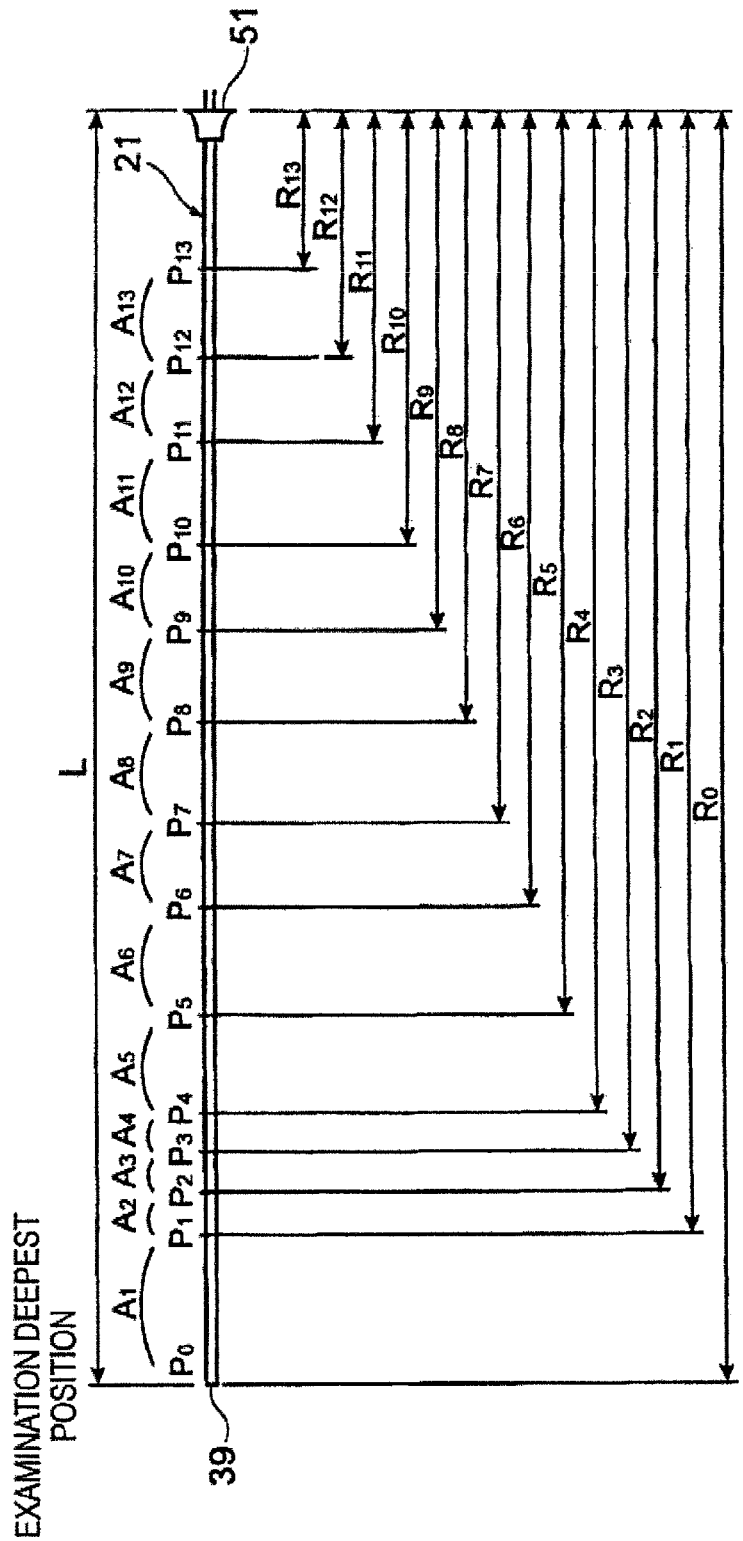
FIG. 21 schematically illustrates a relationship between insertion lengths of the endoscope insertion unit and positions of respective examination parts.

More specifically, the mouth piece 51 is attached to the mouth of a patient before an examination. As shown in FIG. 20, the endoscope insertion unit 21A is inserted into the body cavity of the patient through an opening 51a of the mouthpiece 51.

Figure 19:
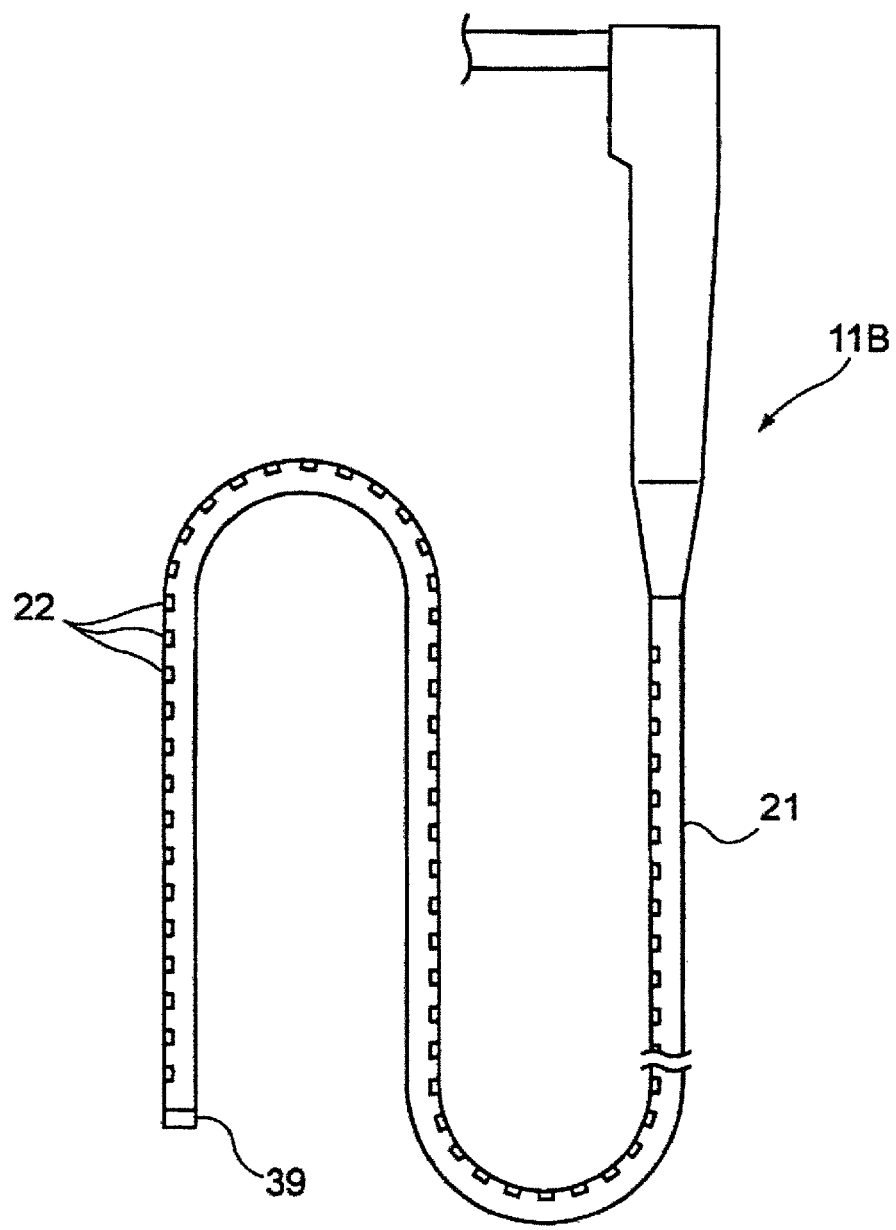
FIG. 19 shows the configuration of an endoscope having a function of detecting an insertion position.

As shown in FIG. 19, the outer circumferential surface of the endoscope insertion unit 21A of the endoscope 11A is provided with marking portions 22 at regular intervals in the longitudinal direction of the endoscope insertion unit 21A. For example, the marking portions 22 are magnetic media. On the other hand, as shown in FIG. 20, the mouthpiece 51 is provided with a sensor 52. Where the marking portions 22 are magnetic media, a magnetic sensor is used as the sensor 52.

In the state that the endoscope insertion unit 21A is inserted in the mouthpiece 51 (see FIG. 20), when the endoscope insertion unit 21A is moved in the body cavity of a patient, the marking portion 22 that is opposed to (and hence is detected by) the sensor 52 varies one after another and pulse electrical signals are thereby output from the sensor 52. A movement length of the endoscope insertion unit 21A from a particular reference position, that is, an insertion length, can be recognized by counting the number of pulses that are output from the sensor 52.

A part (organ) of a living body where the endoscope tip portion 39 is located can be determined from an insertion length of the endoscope insertion unit 21A in the body cavity.

The marking portions 22 and the sensor 25 may be such that a position is detected by reading optical information rather than magnetic information. For example, plural optical information recording media having a different color than the surface color of the endoscope insertion unit 21A are arranged as marking portions on the endoscope insertion unit 21A in its longitudinal direction. The mouthpiece 51 is provided with an optical sensor for reading optical information from each marking portion by illuminating it with light and detecting reflection light. Thus, an insertion length of the endoscope insertion unit 21A can also be detected.

To detect an insertion length of the endoscope insertion unit 21A in a body cavity, it is necessary to take into consideration that the relationship between the position of the endoscope tip portion 39 relative to the mouthpiece 51 (insertion length or distance) and the imaging part varies from one patient to another depending on the age, height, anamneses (e.g., gastroptosis), etc. of the patient. In view of this, a detected insertion length is corrected in advance taking into consideration the age, height, anamneses etc. of the patient and an imaging part is determined using a corrected insertion length. A part of a living body can thus be determined with high accuracy.

An example method for detecting an insertion length of the endoscope insertion unit 21A in a body cavity will be described below. Since the relationship between the insertion length of the endoscope insertion unit 21A is affected by the body shape etc. of the patient, a distance between the mouthpiece 51 and the endoscope tip portion 39 that is detected when the endoscope tip portion 39 has reached the deepest portion in the body cavity is determined as a maximum insertion length L and imaging parts are managed using ratios of insertion lengths to the maximum insertion length L, respectively.

FIG. 18 schematically shows a relationship between insertion lengths of the endoscope insertion unit 21A and positions P0-P13 of respective examination parts in a body cavity. The positions P0-P13 of the examination parts in the body cavity can be represented by insertion lengths of the endoscope insertion unit 21A, respectively. In FIG. 18, the positions P0 -P13 in the body cavity are shown in order, the position P0 being the position of the endoscope tip portion 39 inserted deepest. The insertion lengths of the endoscope insertion unit 21A in the body cavity are represented by their actual ratios R0-R13 to a maximum insertion length L that is equal to the distance between the position of the mouthpiece 51 and the detected examination deepest position P0. For example, the ratio R1 is the ratio L1/L of an insertion length L1 of the endoscope insertion unit 21 from the mouthpiece 51 to the examination position P1 to the maximum insertion length L.

The actual ratios R0-R13 are stored in the endoscope control apparatus 13 as constants. For example, the actual ratios R0-R13 are stored for the 13 (first to 13th) imaging positions shown in Table 1 (used above). The endoscope control apparatus 13 can determine an imaging position corresponding to a current insertion length by comparing a detection ratio which is a ratio of a current insertion length of the endoscope insertion unit 21A to the maximum insertion length L with the individual actual ratios.

Where imaging parts are managed by detecting positions of the endoscope tip portion 39 in the above-described manner, data of still images and a moving image are recorded in the image recording apparatus 200 (see FIG. 14) together with pieces of position information that were detected when the respective still images were taken, that is, detection ratios and pieces of organ discrimination information. In this case, when a shortage in the number of still images taken is detected by the terminal apparatus 300 based on the data recorded in the image recording apparatus 200, an imaging part corresponding to a missing still image can be determined based on pieces of position information that are contained in still images that immediately precede or follow the missing still image. Such pieces of position information can thus be used for assisting addition of a missing still image. Furthermore, an image frame range of data corresponding to an imaging part of a missing still image can be determined by referring to pieces of position information contained in moving image data. Such pieces of position information can thus be used for extracting a necessary still image.

<Fourth Position Determining Method>

When each examination part is imaged with the endoscope insertion unit 21 inserted in the body cavity, the image recording apparatus 200 can record, as part of still image data, a time stamp which is information including a current (i.e., a date and time of imaging). The image recording apparatus 200 can also record, as part of each of a large number of image frames constituting a moving image, a time stamp representing an imaging time. Relative time information such as an elapsed time from an examination (imaging) start time may be recorded instead of an actual time.

Where time stamps are contained in still image data and moving image data that are recorded in the image recording apparatus 200 shown in FIG. 14, the terminal apparatus 300 can use those time stamps to assist addition of missing still images. When the inside of the body cavity of a patient is examined using an endoscope, the examination is usually performed regularly in predetermined order. That is, the imaging part varies as the endoscope tip portion 39 is moved through a body cavity from a deepest portion in the same direction at an approximately constant speed. Therefore, there is a correlation between the actual time or the elapsed time from an examination start time and the imaging part.

Therefore, when a shortage in the number of still images taken is found by the terminal apparatus 300 based on data recorded in the image recording apparatus 200, an imaging part corresponding to a missing still image can be determined from time stamps that are contained in data of still images that precede or follow the missing image. Addition of missing still images can be assisted in this manner Furthermore, a range of image frames that include data corresponding to an imaging part of a missing image can be determined by referring to time stamps contained in respective image frames of moving image data. Thus, processing of extracting necessary still images can also be assisted.

Imaging parts of still images that are missing from recorded still images can be determined with higher accuracy by using at least one of hue changes between images due to differences between imaging subject organs, recognition results of the endoscope insertion unit 21 etc. appearing in images, insertion lengths of the endoscope insertion unit 21, and time stamps representing imaging times and contained in image data or a combination of those kinds of information. Those kinds of information can also be used for determining an image frame of an imaging part corresponding to a missing still image from all image files of moving image data or restricting the range of image frames in extracting data of the missing still image from the moving image data.

Therefore, when a shortage in the number of still images recorded in the image recording apparatus 200 is found, the moving image-still image converting section 310's adding missing still images by extracting them from moving image data automatically or according to instructions from the manipulator can be performed efficiently and correctly.

In the above operation, to assist the operator, it is preferable that the terminal apparatus 300 give, to the operator, through display on the display unit 41, necessary information such as information indicating an imaging part corresponding to a missing still image, hue information of the imaging part corresponding to the missing still image, information indicating whether or not the endoscope insertion unit 21 appears in an image, insertion lengths of the endoscope insertion unit 21, and time stamps. The terminal apparatus 300 may assist the operator by determining an imaging part corresponding to a missing still image in advance and restricting a range of image frames to be extracted among a large number of image frames of moving image data or automatically selecting and displaying a particular image frame to be extracted according to the imaging part determined in advance.

Equipped with the above-described image recording apparatus 200 and terminal apparatus 300, the endoscope mage recording apparatus according to the invention can output a prescribed image acquisition assist signal that will serve for addition of missing still images when a shortage has occurred in the number of still images recorded. Adding missing still image using moving image data that was recorded in an endoscopic examination is particularly effective in lowering the load on the patient. Furthermore, determining an imaging part corresponding to a missing still image or restricting the extraction target range of moving image data using various kinds of information is effective in assisting the operator, whereby the missing still image can be extracted smoothly.

The assist procedure relating to the process of FIG. 16 which is executed by the terminal apparatus 300 may be stored in, for example, the storage unit of the terminal apparatus as an endoscope image recording assisting program, which is activated by a manipulation of the operator of the terminal apparatus 300 and run by a computer incorporated in the terminal apparatus 300.

The invention is not limited to the above embodiment. A person skilled in the art would be able to modify or apply it based on the disclosure of the specification and known techniques, and such modifications and applications are also included in the range of protection. For example, imaging of a moving image need not always be started when a first still image is taken and may be started when the endoscope insertion unit 21 starts to be inserted into a body cavity.

As described above, the following items are disclosed in the specification.

(15) An endoscope image recording apparatus records examination image data including data of still images of a preset, plural number of examination parts based on an image signal which is output from an endoscope when a patient is subjected to an endoscopic examination. The endoscope image recording apparatus includes a data storage unit, a number-of-recorded-images detecting unit, a number-of-images comparing and judging unit and a signal output unit. The data storage unit stores, based on the image data, moving image data representing a moving image and still image data representing still images each of which is imaged upon reception of a prescribed instruction. The number-of-recorded-images detecting unit detects the number of recorded still images from the still image data stored in the data storage unit. The number-of-images comparing and judging unit compares the number of recorded still images detected by the number-of-recorded-images detecting unit with a total number of images which corresponds to the plural examination parts, and judges whether or not the number of recorded still images is smaller than the total number of images. The signal output unit outputs an image acquisition assist signal for acquisition of a missing still image from the moving image data stored in the data storage unit when the number-of-images comparing and judging unit judges that the number of recorded still images is smaller than the total number of images.

This endoscope image recording apparatus makes it possible to assist work of generating missing still images based on moving image data to complete still image data when a shortage in the number of still images of examination parts is found even after completion of an endoscopic examination in which parts that need to be examined are specified in advance. Since still images of all examination parts are always acquired, the accuracy of diagnosis is not lowered and the load on a patient can be reduced (e.g., an endoscopic re-examination for imaging missing images can be avoided).

(16) The endoscope image recording apparatus according to (15), the number-of-recorded-images detecting unit detects the numbers of recorded still images of respective organs by determining an organ to which an examination part corresponding to each of the recorded still images belongs. The number-of-images comparing and judging unit judges whether or not the numbers of recorded still images of the respective organs are in shortage through comparison with total numbers of images of the respective organs.

According to this endoscope image recording apparatus, whether a missing still image has occurred or not can be judged on an organ-by-organ basis because the numbers of recorded still images are detected for respective organs. This facilitates determination of a scene of an examination part corresponding to a still image to be extracted in extracting the still image from moving image data.

(17) The endoscope image recording apparatus according to (16), the number-of-recorded-images detecting unit determines an organ to which an examination part corresponding to each recorded still image belongs based on color information of the recorded still image.

According to this endoscope image recording apparatus, organs that were imaged can be discriminated from each other by detecting, from recorded still images, hues that are characteristic of the respective organs.

(18) The endoscope image recording apparatus according to (16), the number-of-recorded-images detecting unit determines an organ to which an examination part corresponding to each recorded still image belongs based on an insertion length of an insertion unit of the endoscope.

According to this endoscope image recording apparatus, an imaging position can easily be determined from an insertion length of the endoscope insertion unit, that is, an insertion length from the mouth from which the endoscope insertion unit is inserted to the endoscope tip portion. And an organ corresponding to the determined imaging position can easily be determined.

(19) The endoscope image recording apparatus according to (16), the number-of-recorded-images detecting unit determines an organ to which an examination part corresponding to each recorded still image belongs based on a particular image pattern which is extracted from the recorded still image.

According to this endoscope image recording apparatus, when a particular image pattern is extracted from a still image taken, an organ corresponding to the still image can be determined using the particular image pattern. For example, when the cardiac region of stomach as an examination part is imaged, the endoscope tip portion is curved to a large extent and a portion, behind the tip portion, of the endoscope insertion unit is included in the field of view. Therefore, whether or not the examination part that was imaged is the cardiac region of stomach can be determined by detecting whether or not a still image taken includes an image pattern corresponding to the endoscope insertion unit.

(20) The endoscope image recording apparatus according to (16), the number-of-recorded-images detecting unit determines an organ to which an examination part corresponding to each recorded still image belongs based on an imaging time of the recorded still image.

In this endoscope image recording apparatus, where an endoscopic examination is performed in such a manner that examination parts are imaged sequentially as the endoscope insertion unit is pulled out gradually starting from an examination deepest position in a living body after the endoscope tip portion was inserted to the examination deepest position, elapsed times from the start of the examination should correspond to the arrangement of examination parts (organs) in the body cavity. Therefore, an organ that was imaged can be determined based on an imaging time of each still image.

(21) The endoscope image recording apparatus according to any one of (16) to (20), the signal output unit outputs an organ discrimination signal indicating an organ corresponding to the missing still image together with the image acquisition assist signal.

In this endoscope image recording apparatus, an organ discrimination signal indicating an organ corresponding to a missing still image is output together with the image acquisition assist signal. Since the organ discrimination signal indicates from which scene of moving image data a missing still image should be acquired, work of acquiring a necessary still image is made easier.

(22). The endoscope image recording apparatus according to any one of (15) to (21), the data storage unit stores the moving image data together with ID information for identification of the patient. The signal output unit outputs the ID information together with the image acquisition assist signal.

This endoscope image recording apparatus makes it possible to search moving image data stored in the data storage means based on ID information that is output together with an image acquisition assist signal. Therefore, even if moving image data of plural patients are stored in the data storage means, no improper corresponding relationship between a patient and still images is caused.

(23) An endoscope image recording assisting method records examination image data including data of still images of a preset, plural number of examination parts based on an image signal which is output from an endoscope when a patient is subjected to an endoscopic examination. The endoscope image recording assisting method includes: detecting the number of recorded still images from the stored still image data after both of moving image data representing a moving image and still image data representing still images each of which is imaged upon reception of a prescribed instruction are stored based on the image signal; comparing the detected number of recorded still images with a total number of images which corresponds to the plural examination parts; and outputting an image acquisition assist signal for acquisition of a missing still image from the stored moving image data when the number of recorded still images is judged smaller than the total number of images.

(24) A non-transitory computer readable medium causes a computer to execute a process of the endoscope image recording assisting method according to (23).

What is claimed is:

1. An endoscope image recording apparatus for recording examination image data including data of still images of a preset, plural number of examination parts based on an image signal which is output from an endoscope when a patient is subjected to an endoscopic examination, comprising:
    an endoscope control apparatus;
    a data storage unit that stores, based on the image data, moving image data representing a moving image and still image data representing still images each of which is imaged upon reception of a prescribed instruction;
    a number-of-recorded-images detecting unit that detects the number of recorded still images from the still image data stored in the data storage unit;
    a number-of-images comparing and judging unit that compares the number of recorded still images detected by the number-of-recorded-images detecting unit with a total number of images which corresponds to the plural examination parts, and that judges whether or not the number of recorded still images is smaller than the total number of images;
    a signal output unit that outputs an image acquisition assist signal for acquisition of a missing still image from the moving image data stored in the data storage unit when the number-of-images comparing and judging unit judges that the number of recorded still images is smaller than the total number of images; and
    a control section that provides control for the data storage unit, the number-of-recorded images detecting unit, the number-of-images comparing and judging unit, and the signal output unit.

2. The endoscope image recording apparatus according to claim 1, wherein:
    the number-of-recorded-images detecting unit detects the numbers of recorded still images of respective organs by determining an organ to which an examination part corresponding to each of the recorded still images belongs, and
    the number-of-images comparing and judging unit judges whether or not the numbers of recorded still images of the respective organs are in shortage through comparison with total numbers of images of the respective organs.

3. The endoscope image recording apparatus according to claim 2, wherein the number-of-recorded-images detecting unit determines an organ to which an examination part corresponding to each recorded still image belongs based on color information of the recorded still image.

4. The endoscope image recording apparatus according to claim 2, wherein the number-of-recorded-images detecting unit determines an organ to which an examination part corresponding to each recorded still image belongs based on an insertion length of an insertion unit of the endoscope.

5. The endoscope image recording apparatus according to claim 2, wherein the number-of-recorded-images detecting unit determines an organ to which an examination part corresponding to each recorded still image belongs based on a particular image pattern which is extracted from the recorded still image.

6. The endoscope image recording apparatus according to claim 2, wherein the number-of-recorded-images detecting unit determines an organ to which an examination part corresponding to each recorded still image belongs based on an imaging time of the recorded still image.

7. The endoscope image recording apparatus according to claim 2, wherein the signal output unit outputs an organ discrimination signal indicating an organ corresponding to the missing still image together with the image acquisition assist signal.

8. The endoscope image recording apparatus according to claim 1, wherein:
    the data storage unit stores the moving image data together with ID information for identification of the patient, and
    the signal output unit outputs the ID information together with the image acquisition assist signal.

9. An endoscope image recording assisting method for recording examination image data including data of still images of a preset, plural number of examination parts based on an image signal which is output from an endoscope when a patient is subjected to an endoscopic examination, the method comprising:
    detecting the number of recorded still images from the stored still image data after both of moving image data representing a moving image and still image data representing still images each of which is imaged upon reception of a prescribed instruction are stored based on the image signal;
    comparing the detected number of recorded still images with a total number of images which corresponds to the plural examination parts; and
    outputting an image acquisition assist signal for acquisition of a missing still image from the stored moving image data when the number of recorded still images is judged smaller than the total number of images,
    wherein the method is performed by an endoscope control apparatus comprising a control section.

10. A non-transitory computer readable medium causing a computer to execute a process of an endoscope image recording assisting method for recording examination image data including data of still images of a preset, plural number of examination parts based on an image signal which is output from an endoscope when a patient is subjected to an endoscopic examination, the method comprising:
    detecting the number of recorded still images from the stored still image data after both of moving image data representing a moving image and still image data representing still images each of which is imaged upon reception of a prescribed instruction are stored based on the image signal;
    comparing the detected number of recorded still images with a total number of images which corresponds to the plural examination parts; and outputting an image acquisition assist signal for acquisition of a missing still image from the stored moving image data when the number of recorded still images is judged smaller than the total number of images.

* * * * *